US009968698B2

(12) United States Patent
Whitten et al.

(10) Patent No.: US 9,968,698 B2
(45) Date of Patent: May 15, 2018

(54) CHARGED SINGLET-OXYGEN SENSITIZERS AND OPPOSITELY-CHARGED SURFACTANTS

(71) Applicant: STC.UNM, Albuquerque, NM (US)

(72) Inventors: David G. Whitten, Albuquerque, NM (US); Eric H. Hill, Albuquerque, NM (US); Harry C. Pappas, Albuquerque, NM (US)

(73) Assignee: STC. UNM, Albuquerque, NM (US)

( * ) Notice: Subject to any disclaimer, the term of this patent is extended or adjusted under 35 U.S.C. 154(b) by 336 days.

(21) Appl. No.: 14/533,612

(22) Filed: Nov. 5, 2014

(65) Prior Publication Data

US 2015/0132184 A1     May 14, 2015

Related U.S. Application Data

(60) Provisional application No. 61/902,057, filed on Nov. 8, 2013, provisional application No. 61/903,811, filed on Nov. 13, 2013.

(51) Int. Cl.
| *A61L 2/18* | (2006.01) |
| *A01N 41/04* | (2006.01) |
| *A01N 33/12* | (2006.01) |

(52) U.S. Cl.
CPC ............ *A61L 2/18* (2013.01); *A01N 33/12* (2013.01); *A01N 41/04* (2013.01)

(58) Field of Classification Search
CPC .................................. A61L 2/18; A01N 33/12
See application file for complete search history.

(56) References Cited

U.S. PATENT DOCUMENTS

| 4,251,386 A | 2/1981 | Saeki et al. |
| 5,449,809 A | 9/1995 | Wingert et al. |
| 5,489,400 A | 2/1996 | Liu et al. |
| 6,743,640 B2 | 6/2004 | Whitten et al. |
| 6,841,669 B2 | 1/2005 | Cipriani et al. |
| 7,122,383 B2 | 10/2006 | Jones et al. |
| 8,455,265 B2 | 6/2013 | Whitten et al. |
| 8,598,053 B2 | 12/2013 | Whitten et al. |
| 8,618,009 B2 | 12/2013 | Schanze et al. |
| 8,753,570 B2 | 6/2014 | Whitten et al. |
| 9,005,540 B2 | 4/2015 | Schanze et al. |
| 9,125,415 B2 | 9/2015 | Schanze et al. |
| 2003/0134959 A1 | 7/2003 | Hancock et al. |
| 2003/0168756 A1 | 9/2003 | Balkus, Jr. et al. |
| 2003/0178607 A1 | 9/2003 | Swager et al. |
| 2004/0241768 A1 | 12/2004 | Whitten et al. |
| 2005/0059168 A1 | 3/2005 | Bazan et al. |
| 2005/0148254 A1 | 7/2005 | Lu et al. |
| 2006/0120923 A1 | 6/2006 | Swager et al. |
| 2006/0175193 A1 | 8/2006 | Inganas et al. |
| 2007/0215841 A1 | 9/2007 | Ford et al. |
| 2008/0090021 A1 | 4/2008 | Long et al. |
| 2010/0035948 A1 | 2/2010 | Kumar et al. |
| 2011/0159605 A1 | 6/2011 | Whitten et al. |
| 2011/0223058 A1 | 9/2011 | Whitten et al. |
| 2011/0293470 A1 | 12/2011 | Schanze et al. |
| 2012/0271023 A1 | 10/2012 | Whitten et al. |
| 2013/0210828 A1 | 8/2013 | Whitten et al. |
| 2013/0273800 A1 | 10/2013 | Whitten et al. |
| 2013/0330386 A1 | 12/2013 | Whitten et al. |
| 2014/0086795 A1 | 3/2014 | Schanze et al. |
| 2014/0242148 A1 | 8/2014 | Whitten et al. |
| 2014/0341776 A1 | 11/2014 | Schanze et al. |

FOREIGN PATENT DOCUMENTS

| JP | 3198365 B2 | 8/2001 |
| WO | WO-2008143731 A2 | 11/2008 |
| WO | WO-2009158606 A2 | 12/2009 |
| WO | WO-2009158606 A9 | 12/2009 |
| WO | WO-2010044743 A1 | 4/2010 |
| WO | WO-2010054304 A2 | 5/2010 |
| WO | WO-2011044580 A3 | 4/2011 |
| WO | WO-2012009472 A2 | 1/2012 |
| WO | WO-2012079085 A2 | 6/2012 |
| WO | WO-2012009484 A2 | 11/2012 |
| WO | WO-2013020096 A2 | 2/2013 |
| WO | WO-2013020096 A3 | 2/2013 |

(Continued)

OTHER PUBLICATIONS

Tan et al. Thermodynamics of Sodium Dodecyl Sulfate Partitioning into Lipid Membranes. Biophysics Journal vol. 83 p. 1547-56. Sep. 2002.*
"U.S. Appl. No. 13/809,573, Non Final Office Action dated Aug. 25, 2016", 13 pgs.
"U.S. Appl. No. 13/809,573, Response filed Apr. 22, 2016 to Non-Final Office Action dated Jan. 22, 2016", 13 pgs.
"U.S. Appl. No. 13/809,573, Response filed Sep. 22, 2016 to Non-Final Office Actino dated Aug. 25, 2016", 18 pgs.
"PubChem. Substance Record for SID 76464254", Retrieved from the Internet. <URL: https://pubchem.ncbi.nlm.nih.gov/substance/76464254#section=Top>, (Jun. 12, 2009), 5 pgs.
"U.S. Appl. No. 12/529,390, Examiner Interview Summary dated Jan. 31, 2012", 3 pgs.
"U.S. Appl. No. 12/529,390, Examiner Interview Summary dated Nov. 13, 2012", 3 pgs.
"U.S. Appl. No. 12/529,390, Non Final Office Action dated Jul. 18, 2012", 7 pgs.
"U.S. Appl. No. 12/529,390, Non-Final Office Action dated Nov. 1, 2011", 11 pgs.
"U.S. Appl. No. 12/529,390, Notice of Allowance dated Feb. 5, 2013", 10 pgs.
"U.S. Appl. No. 12/529,390, Preliminary Amendment dated Sep. 1, 2009", 13 pgs.

(Continued)

*Primary Examiner* — Donald R Spamer
(74) *Attorney, Agent, or Firm* — Schwegman Lundberg & Woessner, P.A.

(57) ABSTRACT

The invention relates to compositions including a charged oligo-phenylene ethynylene singlet-oxygen sensitizer and an oppositely-charged surfactant, which show an enhanced biocidal activity relative to a comparable concentration of the oligo-phenylene ethynylene without the oppositely-charged surfactant. The enhancement of biocidal activity is observed with an anionic oligo-phenylene ethynylene in the presence of a cationic surfactant such as TTAB, and with a cationic oligo-phenylene ethynylene in the presence of an anionic surfactant such as SDS.

8 Claims, 14 Drawing Sheets
(14 of 14 Drawing Sheet(s) Filed in Color)

(56) References Cited

FOREIGN PATENT DOCUMENTS

WO  WO-2013055417 A2  4/2013
WO  WO-2013055417 A3  4/2013

OTHER PUBLICATIONS

"U.S. Appl. No. 12/529,390, Response filed May 1, 2012 to Non Final Office Action dated Nov. 1, 2011", 19 pgs.
"U.S. Appl. No. 12/529,390, Response filed Dec. 18, 2012 to Non Final Office Action dated Jul. 18, 2012", 16 pgs.
"U.S. Appl. No. 13/001,478, Response filed Dec. 19, 2013 to Non Final Office Action dated Oct. 3, 2013", 10 pgs.
"U.S. Appl. No. 13/001,478, Non Final Office Action dated Oct. 3, 2013", 6 pgs.
"U.S. Appl. No. 13/001,478, Notice of Allowance dated Jan. 31, 2014", 7 pgs.
"U.S. Appl. No. 13/001,478, Response filed Jul. 11, 2013 to Restriction Requirement dated Jun. 13, 2013", 9 pgs.
"U.S. Appl. No. 13/001,478, Restriction Requirement dated Jun. 13, 2013", 7 pgs.
"U.S. Appl. No. 13/128,571, Response filed Nov. 19, 2012 to Restriction Requirement dated Oct. 17, 2012", 6 pgs.
"U.S. Appl. No. 13/128,571, Non Final Office Action dated Feb. 13, 2013", 10 pgs.
"U.S. Appl. No. 13/128,571, Notice of Allowance dated Aug. 28, 2013", 9 pgs.
"U.S. Appl. No. 13/128,571, Preliminary Amendment filed May 10, 2011", 5 pgs.
"U.S. Appl. No. 13/128,571, Response filed May 13, 2013 to Non Final Office Action dated Feb. 13, 2013", 12 pgs.
"U.S. Appl. No. 13/128,571, Restriction Requirement dated Oct. 17, 2012", 6 pgs.
"U.S. Appl. No. 13/503,067, Response filed Mar. 11, 2013 to Non Final Office Action dated Oct. 10, 2012", 11 pgs.
"U.S. Appl. No. 13/503,067, Response filed Jul. 11, 2013 to Final Office Action dated Jun. 6, 2013", 7 pgs.
"U.S. Appl. No. 13/503,067, Final Office Action dated Jun. 6, 2013", 11 pgs.
"U.S. Appl. No. 13/503,067, Non Final Office Action dated Oct. 10, 2012", 11 pgs.
"U.S. Appl. No. 13/503,067, Notice of Allowance dated Aug. 2, 2013", 10 pgs.
"U.S. Appl. No. 13/809,573, Non Final Office Action dated Jan. 22, 2016", 13 pgs.
"U.S. Appl. No. 13/809,573, Preliminary Amendment filed Jan. 10, 2013", 9 pgs.
"U.S. Appl. No. 13/809,573, Response filed Sep. 24, 2015 to Restriction Requirement dated Jul. 24, 2015", 9 pgs.
"U.S. Appl. No. 13/809,573, Restriction Requirement dated Jul. 24, 2015", 7 pgs.
"U.S. Appl. No. 13/993,026 Response filed Sep. 8, 2015 to Final Office Action dated Jun. 8, 2015", 10 pgs.
"U.S. Appl. No. 13/993,026, Final Office Action dated Jun. 8, 2015", 15 pgs.
"U.S. Appl. No. 13/993,026, Non Final Office Action dated Jan. 27, 2015", 9 pgs.
"U.S. Appl. No. 13/993,026, Preliminary Amendment filed Jun. 10, 2013", 7 pgs.
"U.S. Appl. No. 13/993,026, Response filed Apr. 9, 2015 to Non Final Office Action dated Jan. 27, 2015", Response to Non Final Office Action, 11 pgs.
"U.S. Appl. No. 14/092,409, Notice of Allowance dated Dec. 10, 2014", 10 pgs.
"U.S. Appl. No. 14/127,465, Non Final Office Action dated Jan. 21, 2015", 4 pgs.
"U.S. Appl. No. 14/127,465, Notice of Allowance dated Apr. 30, 2015", 7 pgs.
"U.S. Appl. No. 14/127,465, Response filed Apr. 20, 2015 to Non Final Office Action dated Jan. 21, 2015", 9 pgs.

"European Application Serial No. 09771137.8, Office Action dated Feb. 9, 2011", 1 pg.
"European Application Serial No. 09771137.8, Office Action dated Feb. 14, 2011", 2 pgs.
"European Application Serial No. 09771137.8, Office Action dated Mar. 3, 2011", 1 pg.
"European Application Serial No. 09771137.8, Office Action dated Mar. 16, 2011", 1 pg.
"European Application Serial No. 09771137.8, Response filed Feb. 18, 2011 to Office Action dated Feb. 9, 2011", 6 pgs.
"International Application Serial No. PCT/US2008/002756, International Preliminary Report on Patentability dated Sep. 1, 2009", 6 pgs.
"International Application Serial No. PCT/US2008/002756, International Search Report dated Feb. 25, 2009", 2 pgs.
"International Application Serial No. PCT/US2008/002756, Written Opinion dated Feb. 25, 2009", 5 pgs.
"International Application Serial No. PCT/US2009/048838, International Preliminary Report on Patentability dated Jan. 5, 2011", 7 pgs.
"International Application Serial No. PCT/US2009/048838, International Search Report dated Apr. 30, 2010", 4 pgs.
"International Application Serial No. PCT/US2009/048838, Written Opinion dated Apr. 30, 2010", 6 pgs.
"International Application Serial No. PCT/US2009/063715, International Preliminary Report on Patentability dated May 10, 2011", 6 pgs.
"International Application Serial No. PCT/US2009/063715, International Search Report dated May 27, 2010", 4 pgs.
"International Application Serial No. PCT/US2009/063715, Written Opinion dated May 27, 2010", 5 pgs.
"International Application Serial No. PCT/US2010/052332, International Preliminary Report on Patentability dated Apr. 11, 2012", 7 pgs.
"International Application Serial No. PCT/US2010/052332, International Search Report dated Jun. 24, 2011", 4 pgs.
"International Application Serial No. PCT/US2010/052332, Written Opinion dated Jun. 24, 2011", 6 pgs.
"International Application Serial No. PCT/US2011/043908, International Preliminary Report on Patentability dated Jan. 15, 2013", 7 pgs.
"International Application Serial No. PCT/US2011/043908, International Search Report and Written Opinion dated Apr. 6, 2012", 11 pgs.
"International Application Serial No. PCT/US2011/043922, International Preliminary Report on Patentability dated Jan. 15, 2013", 4 pgs.
"International Application Serial No. PCT/US2011/043922, International Search Report dated Mar. 19, 2012", 3 pgs.
"International Application Serial No. PCT/US2011/043922, Written Opinion dated Mar. 19, 2012", 3 pgs.
"International Application Serial No. PCT/US2011/064460, International Preliminary Report on Patentability dated Jun. 20, 2013", 7 pgs.
"International Application Serial No. PCT/US2011/064460, International Search Report dated Jun. 19, 2012", 6 pgs.
"International Application Serial No. PCT/US2011/064460, Written Opinion dated Jun. 19, 2012", 5 pgs.
"International Application Serial No. PCT/US2012/045598, International Preliminary Report on Patentability dated Jan. 23, 2014", 6 pgs.
"International Application Serial No. PCT/US2012/045598, International Search Report dated May 27, 2013", 3 pgs..
"International Application Serial No. PCT/US2012/045598, Written Opinion dated May 27, 2013", 4 pgs.
"International Application Serial No. PCT/US2012/049613, International Preliminary Report on Patentability dated Feb. 13, 2014", 9 pgs.
"International Application Serial No. PCT/US2012/049613, International Search Report dated Feb. 26, 2013", 3 pgs.
"International Application Serial No. PCT/US2012/049613, Written Opinion dated Feb. 26, 2013", 7 pgs.

(56) References Cited

OTHER PUBLICATIONS

"International Application Serial No. PCT/US2015/020546, International Search Report dated Aug. 10, 2015", 4 pgs.
"International Application Serial No. PCT/US2015/020546, Invitation to Pay Additional Fees and Partial Search Report dated May 20, 2015", 2 pgs.
"International Application Serial No. PCT/US2015/020546, Written Opinion dated Aug. 10, 2015", 5 pgs.
Addinall, Stephen, et al., "Temperature Shift Experiments with an ftsZ84(Ts) Strain Reveal Rapid Dynamics of FtsZ Localization and Indicate hat the Z Ring Is Required throughout Septation and Cannot Reoccupy Division Sites Once Constriction Has Initiated", J. of Bacteriology, vol. 179, No. 13, (1997), 4277-4284.
Ambade, A. V, et al., "Fluorescent Polyelectrolytes as Protein Sensors", in: Polym. Int., 2007, vol. 56, (2007), 474-481.
Anderson, David E, et al., "Assembly Dynamics of FtsZ Rings in Bacillus subtilis and *Escherichia coli* and Effects of FtsZ-Regulating Proteins", Journal of Bacteriology, 186(17)., (2004), 5775-5781.
Antoci, Jr., Valentin, et al., "Vancomycin covalently bonded to titanium alloy prevents bacterial colonization", Journal of Orthopaedic Research, 25(7), (2007), 858-866.
Arnt, Lachelle, et al., "Cationic Facially Amphiphilic Poly(phenylene ethynylene)s Studied at the Air-Water Interface", Langmuir, 19(6), (2004), 2404-2408.
Arnt, Lachelle, et al., "New Poly(phenyleneethynylene)s with Cationic, Facially Amphiphilic Structures", Journal of the American Chemical Society, 124(26), (2002), 7664-7665.
Arnt, Lachelle, et al., "Nonhemolytic Abiogenic Polymers as Antimicrobial Peptide Mimics", J. Polym. Sci., Part A: Polym. Chem., 42(15), (2004), 3860-3864.
Bartlett, Grant R., "Phosphorus Assay in Column Chromatography", The Journal of Biological Chemistry, 234(3), (1959), 466-468.
Beaujuge, Pierre M., et al., "Spectral Engineering in pie-Conjugated Polymers with Intramolecular Donor-Acceptor Interactions", Accounts of Chemical Research, 43(11), (Nov. 2010), 1396-1407.
Beckloff, Nicholas, et al., "Activity of an Antimicrobial Peptide Mimetic against Planktonic and Biofilm Cultures of Oral Pathogens", Antimicrobial Agents and Chemotherapy, 51, (2007), 4125-4132.
Boeneman, Kelly, et al., "*Escherichia coli* DnaA forms helical structures along the longitudinal cell axis distinct from MreB ?laments", Molecular Microbiology, 72(3)., (2009), 645-657.
Bruns, R., et al., "Chapter 3—R&D in material protection: New biocides", in: Directory of Microbicides for the Protection of Materials—A Handbook, Paulus, W., Editor, (2005), 25-46.
Buffet-Bataillon, Sylvie, et al., "Emergence of resistance to antibacterial agents: the role of quaternary ammonium compounds—a critical review", International Journal of Antimicrobial Agents, 39(5)., (2012), 381-389.
Burton, Paul, et al., "Two Pathways of Division Inhibition in UV-Irradiated *E. coli*", Mol Gen Genet., 190(1)., (1983), 128-132.
Cabiscol, Elisa, et al., "Oxidative stress in bacteria and protein damage by reactive oxygen species", International Microbiology, 3., (2000), 3-8.
Capuano, Ben, et al., "The Synthesis and Preliminary Pharmacological Evaluation of a Series of Substituted 4'-Phenoxypropyl Analogues of the Atypical Antipsychotic Clozapine", Aust. J. Chem., 63, (2010), 116-124.
Ceri, H., et al., "The Calgary Biofilm Device: New Technology for Rapid Determination of Antibiotic Susceptibilities of Bacterial Biofilms", Journal of Clinical Microbiology, 37(6), (1999), 1771-1776.
Chamchod, Farida, et al., "Modeling methicillin-resistant *Staphylococcus aureus* in hospitals: Transmission dynamics, antibiotic usage and its history", Theor Biol Med Model. , 9, 25., (2012), 1-14.
Chemburu, Sireesha, et al., "Light-Induced Biocidal Action of Conjugated Polyelectrolytes Supported on Colloids", Langmuir, 24, (2008), 11053-11062.

Choi, W. S., et al., "Synthesis of Two Types of Nanoparticles in Polyelectrolyte Capsule Nanoreactors and Their Dual Functionality", J. Am. Chem. Soc., 127, (2005), 16136-16142.
Clark, A. P. Z., et al., "An Amphiphilic Poly(phenylene ethynylene) as the Structure-Directing Agent for Periodic Nanoscale Silica Composite Materials", Nano Letters, 5, (2005), 1647-1652.
Cooper, B S, et al., "Methicillin-resistant *Staphylococcus aureus* in hospitals and the community: Stealth dynamics and control catastrophes", Proc. Nat. Acad. Sci., 2004, 101(27),, (2004), 10223-10228.
Corbitt, Thomas, et al., "Antimicrobial Non-Woven Fibrous Materials", U.S. Appl. No. 61/528,603, filed Aug. 29, 2011, 17 pgs.
Corbitt, Thomas S., et al., "Conjugated Polyelectrolyte Capsules: Light-Activated Antimicrobial Micro "Roach Motels"†", ACS Appl. Mater. Interfaces, 1(1), (2009), 48-52.
Corbitt, Thomas S., et al., "Light and dark biocidal activity of cationic poly(arylene ethynylene) conjugated polyelectrolytes", Photochem. Photobiol. Sci., 8, (2009), 998-1005.
Costerton, J. William, et al., "Mechanism of Electrical Enhancement of Efficacy of Antibiotics in Killing Biofilm Bacteria", Antimicrobial Agents and Chemotherapy, 38(12), (1994), 2803-2809.
Cramton, Sarah, et al., "The Intercellular Adhesion (ica) Locus Is Present in *Staphylococcus aureus* and Is Required for Biofilm Formation", Infection and Immunity, 67(10)., (1999), 5427-5433.
Dascier, Dimitri, et al., "Efficacy of End-Only-Functionalized Oligo(arylene-ethynylene)s in Killing Bacterial Biofilms", Langmuir, 28(31), (2012), 11286-11290.
De Geest, B. G., et al., "Release mechanisms for polyelectrolyte capsules", Chem. Soc. Rev., 36, (2007), 636-649.
Ding, Liping, et al., "Insight into the Mechanism of Antimicrobial Poly(phenylene ethynylene) Polyelectrolytes: Interactions with Phosphatidylglycerol Lipid Membranes", Langmuir, 25(24), (2009), 13742-13751.
Donlan, Rodney M., et al., "Microbial Life on Surfaces", Emerging Infectious Diseases, 8(9), (2002), 881-890.
Eun, Ye-Jin, et al., "Fabrication of Microbial Biofilm Arrays by Geometric Control of Cell Adhesion", Langmuir, 25(8), (2009), 4643-4654.
Evans, D, et al., "Critical Micelle Concentrations for Alkyltrimethylammonium Bromides in Water from 25 to 160° C.", J. Solution Chem., 13(2)., (1984), 87-101.
Fan, Qu-Li, et al., "Water-Soluble Cationic Poly(p-phenyleneethynylene)s (PPEs): Effects of Acidity and Ionic Strength on Optical Behavior.", Macromolecules.vol. 38, (2005), 2927-2936.
Fang, Zhen, et al., "Low-Bandgap Donor-Acceptor Conjugated Polymer Sensitizers for Dye-Sensitized Solar Cells", Journal of the American Chemical Society, 133(9), (2011), 3063-3069.
Ferreira, Isabel C.F.R, et al., "Screening of antimicrobial activity of diarylamines in the 2,3,5-trimethylbenzo[b]thiophene series a structure-activity evaluation study", Bioorganic & Medicinal Chemistry Letters, 14(23), (2004), 5831-5833.
Flemming, Hans-Curt, et al., "The biofilm matrix", Nat Rev Microbial., 8(9)., (2010), 623-633.
Galaev, Igor Y., "'Smart' polymers in biotechnology and medicine", Russian Chemical Reviews, 64(5), (1995), 471-489.
Gao, Yuan, et al., "Recent Advances in Antimicrobial Treatments of Textiles", Textile Research Journal vol. 78(1), 60-72.
Gao, Yuan, et al., "Recent Advances in Antimicrobial tTreatment of Textiles", Textile Research Journal, 78(1), (2008), 60-72.
George, Wayne N., et al., "Amplified fluorescence quenching in high ionic strength media.", Soft Matter. vol. 3, (2007), 1381-1387.
Gilbert, P, el. al., "Biofilms in vitro and in vivo: do singular mechanism imply cross-resistance?", J Appl Microbiol.,92 Suppl., (2002), 98S-110S.
Goehring, Nathan, et al., "Diverse Paths to Midcell: Assembly of the Bacterial Cell Division Machinery", Current Biology, 15., (2005), R514-R526.
Gorwitz, R, et al., "More Challenges in the Prevention and Management of Community-Associated, Methicillin-Resistant *Staphylococcus aureus* Skin Disease", Ann. Intern. Med., 148 (4)., (2008), 310-312.

(56) References Cited

OTHER PUBLICATIONS

Guan, Bin, et al., "Different Functionalization of the Internal and External Surfaces in Mesoporous Materials for Biosensing Applications Using "Click" Chemistry", Langmuir, 27(1), (2010), 328-334.

Harrison, Joe J., et al., "Microtiter susceptibility testing of microbes growing on peg lids: a miniaturized biofilm model for high-throughput screening", Nature Protocols, 5(7), (2010), 1236-1254.

Hill, Eric, et al., "Cationic oligo-p-phenylene ethynylenes form complexes with surfactants for long-term light-activated biocidal applications", Photochem. Photobiol. Sci., 13., (2014), 247-253.

Hill, Eric, et al., "Photochemistry of "End-Only" Oligo-p-phenylene Ethynylenes: Complexation with Sodium Dodecyl Sulfate Reduces Solvent Accessibility", Langmuir, 29(31), (2013), 9712-9720.

Hoffman, Allan S., "Bioconjugates of Intelligent Polymers and Recognition Proteins for Use in Diagnostics and Affinity Separations", Clinical Chemistry, 46:9, (2000), 1478-1486.

Hortholary, Cedric, et al., "An Approach to Long and Unsubstituted Molecular Wires:? Synthesis of Redox-Active, Cationic Phenylethynyl Oligomers Designed for Self-Assembled Monolayers", J. Org. Chem., 68(6), (2003), 2167-2174.

Huisgen, Rolf, "Centenary Lecture—1,3-Dipolar Cycloadditions", Proceedings of the Chemical Society of London, (Oct. 1961), 357-369.

Ibraeva, Zhanar E., et al., "Solution Properties and Complexation of Polyampholytes based on N,N-Dimethyldiallyl-ammonium Chloride and Maleic Acid or Alkyl (Aryl) Derivatives of Malemic Acids", Macromol. Chem. Phys., 205, (2004), 2464-2472.

Ista, Linnea K., et al., "Conjugated-Polyelectrolyte-Grafted Cotton Fibers Act as "Micro Flypaper" for the Removal and Destruction of Bacteria", ACS Applied Materials & Interfaces, 3(8), (2011), 2932-2937.

Ji, E., "Conjugated polyelectrolytes: Synthesis, photophysical studies and applications to sensors and biocidal activity", Ph.D. dissertation, Univ. of Florida, 2009, (2009), 167 pgs.

Ji, E., et al., "pH-Dependent Optical Properties of a Poly(phenylene ethynylene) Conjugated Polyampholyte", in: Langmuir, vol. 27, (Dec. 28, 2010), 1565-1568.

Ji, Eunkyung, et al., "Antibacterial Activity of Conjugated Polyelectrolytes with Variable Chain Lengths", Langmuir, 27, (2011), 10763-10769.

Ji, Eunkyung, et al., "Light and Dark-Activated Biocidal Activity of Conjugated Polyelectrolytes", ACS Applied Materials & Interfaces, 3(8), (2011), 2820-2829.

Jiang, Hui, et al., "Conjugated Polyelectrolytes: Synthesis, Photophysics, and Applications", Angew. Chem. Int. Ed., 48(24), (2009), 4300-4316.

Jiang, Hui, et al., "Effects of Polymer Aggregation and Quencher Size on Amplified Fluorescence Quenching of Conjugated Polyelectrolytes", Langmuir, 23(18), (2007), 9381-9486.

Jones, Tineke, "Response of *Escherichia Coli* to Environmental Stress", Stress Response of Foodborne Microorganisms. NovaScience Publishers., (2012), 293-330.

Kenawy, El-Refaie, et al., "The Chemistry and Applications of Antimicrobial Polymers: A State-of-the-Art Review", Biomacromolecules, 8(5), (2007), 1359-1384.

Kim, Chae Kyu, et al., "Complexation of Anionic Conjugated Polyelectrolyte with Cationic Surfactant", Macromolecular Research, vol. 13 No. 5, (2005), 460-462.

Klevens, R M, et al., "Estimating Health Care-Associated Infections and Deaths in U.S. Hospitals", Public Health Rep., 2007, 122(2)., (2002), 160-166.

Kolb, Hartmuth C., et al., "Click Chemistry: Diverse Chemical Function from a Few Good Reactions", Angew. Chem. Int. Ed., 40, (2001), 2004-2021.

Kotz, Joachim, "Inter- and intramolecular interactions in polyelectrolyte complex formation with polyampholytes", Macromolecular Chemistry and Physics, 194(2), (1993), 397-410.

Kruse, T, et al., "Dysfunctional MreB inhibits chromosome segregation in *Escherichia coli*", Embo J., 22(19)., (2003), 5283-5292.

Leach, Michelle K., et al., "Electrospinning Fundamentals: Optimizing Solution and Apparatus Parameters", Journal of Visualized Experiments, 47, (2011), 4 pgs.

Lee, H., et al., "Shell Cross-Linked Hyaluronic Acid/Polylysine Layer-by-Layer Polyelectrolyte Microcapsules Prepared by Removal of Reducible Hyaluronic Acid Microgel Cores", Biomacromolecules, 8, (2007), 3705-3711.

Lee, Wen-Fu, et al., "Synthesis and solubility of the poly(sulfobetaine)s and the corresponding cationic polymers: 2. Aqueous solution properties of poly[ N,N'-dimethyl-(acrylamido propyl) ammonium propane sulfonate]", Polymer, 36(2), (1995), 357-364.

Leid, Jeff, et al., "Human Leukocytes Adhere to Penetrate, and Respond to *Staphylococcus aureus* Bio?lms", Infection and Immunity, 70(11)., (2002), 6339-6345.

Lin, Ching-Yao, et al., "Design and Characterization of Novel Porphyrins with Oligo(phenylethylnyl) Links of Varied Length for Dye-Sensitized Solar Cells: Synthesis and Optical, Electrochemical, and Photovoltaic Investigation", J. Phys. Chem. C., 113(2), (2009), 755-764.

Lindig, Barbara, et al., "Determination of the Lifetime of Singlet Oxygen in D20 Using 9, IO-Anthracenedipropionic Acid, a Water-Soluble Probe", J. Am. Chem. Soc., 102 (17)., (1980), 5590-5593.

Lindsay, D., et al., "Bacterial biofilms within the clinical setting: what healthcare professionals should know", Journal of Hospital Infection, 64, (2006), 313-325.

Liu, Yan, et al., "Conjugated polyelectrolytes as fluorescent sensors", Journal of Photochemistry and Photobiology C: Photochemistry Reviews, 10(4), (2009), 173-190.

Lock, Rowena, et al., "Cell-division inhibitors: new insights for Future anibiotics", Nature Reviews Drug Discovery, 7., (2008), 324-338.

Lowe, Andrew B., et al., "Synthesis and Solution Properties of Zwitterionic Polymers", Chem. Rev., 102, (2002), 4177-4189.

Lu, L., et al., "Biocidal Activity of a Light-Absorbing Fluorescent Conjugated Polyelectrolyte", Langmuir, 21, (2005), 10154-10159.

Lu, Timothy K., et al., "Dispersing biofilms with engineered enzymatic bacteriophage", Proc. Natl. Acad. Sci. USA, 104(27), (2007), 11197-11202.

Maciag-Dorszynska, Monika, et al., "Mutations in central carbon metabolism genes suppress defects in nucleoid position and cell division of replication mutants in *Escherichia coli*", Gene 503., (2012), 31-35.

Magrex-Debar, Elisabeth, et al., "Evaluation of biohazards in dehydrated bio?lms", International Journal of Food Microbiology 55., (2000), 239-243.

Mah, Thien-Fah, et al., "Mechanisms of biofilm resistance to antimicrobial agents", TRENDS in Microbiology vol. 9 No. 1., (2001), 34-39.

Malik, Zvi, et al., "New Trends in Photobiology (Invited Review) Bactericidal Effects of Photoactivated Porphyrins—An Alternative Approach to Antimicrobial Drugs", Journal of Photochemistry and Photobiology B: Biology, 5(3-4)., (1990), 281-293.

Mann, Ethan, et al., "Modulation of eDNA Release and Degradation Affects *Staphylococcus aureus* Biofilm Maturation", PLOS One, 4(6)., (2009), e5822.

McCormick, C. L., "Polyampholytes (Overview)", in: Polymeric Materials Encyclopedia, vol. 7, CRC Press, Boca Raton, FL, (1996), 5462-5476.

McNeill, Karol, et al., "Acid tolerance response of bio¢lm cells of *Streptococcus mutans*", FEMS Microbiology Letters, 221., (2003), 25-30.

McQuade, D. Tyler, et al., "Signal Amplification of a"Turn-on Sensor: Harvesting the Light Captured by a Conjugated Polymer, J. Am. Chem. Soc., 122, (2000), 12389-12390.

Neuhaus, Francis, et al., "A Continuum of Anionic Charge: Structures and Functions of D-Alanyl-Teichoic Acids in Gram-Positive Bacteria", Microbiology and Molecular Biology Reviews, 67(4)., (2003), 686-723.

(56) References Cited

OTHER PUBLICATIONS

Nickerson, Emma, et al., "*Staphylococcus aureus* disease and drug resistance in resource-limited countries in south and east Asia", Lancet Infect. Dis., 9., (2009), 130-135.

Nikaido, Hiroshi, "Outer Membrane", *Escherichia coli* and *Salmonella*: cellular and molecular biology. 2nd ed. Washington, D.C: American Society for Microbiology., (1996), 29-47.

Notestein, Justin M., et al., "Covalent Grafting of m-Phenylene-Ethynylene Oligomers to Oxide Surfaces", Chem. Mater., 22, (2010), 5319-5327.

Ogawa, Katsu, et al., "Conjugated Polyelectrolyte-Grafted Silica Microspheres", Langmuir, 23(8), (2007), 4541-4548.

Olson, Merle E., et al., "Biofilm bacteria: formation and comparative susceptibility to antibiotics", Canadian Journal of Veterinary Research-Revue Canadienne De Recherche Veterinaire, 66, (2002), 86-92.

Pasquier, Nicolas, et al., "From Multifunctionalized poly(ethylene Imine)s toward Antimicrobial Coatings", Biomacromolecules, 8, (2007), 2874-2882.

Patel, Dinesh G., et al., "It Takes More Than an Imine: The Role of the Central Atom on the Electron-Accepting Abilitty of Benzotriazole and Benzothiadiazole Oligomers", Journal of the American Chemical Society, 134(5), (2012), 2599-2612.

Pinto, Mauricio R., et al., "Amplified fluorescence sensing of protease activity with conjugated polyelectrolytes", Proc. Natl. Acad. Sci. USA, 101(20), (2004), 7505-7510.

Pinto, Mauricio R., et al., "Conjugated Polyelectrolytes: Synthesis and Applications", Synthesis, 9, (2002), 1293-1309.

Potera, Carol, "C. Microbiology—Forging a Link Between Biofilms and Disease", Science, 283(5409), (1999), 1837-1939.

Reddinger, Jerry L., et al., "Molecular Engineering of p-Conjugated Polymers", Radical Polymerisation Polyelectrolytes, Series: Advances in Polymer Science, vol. 145, (1999), 57-122.

Rice, Kelly, et al., "The cidA murein hydrolase regulator contributes to DNA release and biofilm development in *Staphylococcus aureus*", Proc. Nat. Acad. Sci., 104(19)., (2007), 8113-8118.

Rico, Ana Isabel, et al., "Role of *Escherichia coli* FtsN protein in the assembly and stability of the cell division ring", Molecular Microbiology, 76(3)., (2010), 760-771.

Rolinson, George, "Forty years of β-lactam research", Journal of Antimicrobial Chemotherapy, 41., (1998), 589-603.

Romberg, Laura, et al., "Assembly Dynamics of the Bacterial Cell Division Protein FTSZ: Poised at the Edge of Stability", Annual Review of Microbiology, 57., (2003), 125-154.

Ron, Eliora, et al., "Growth Rate of *Escherichia coli* at Elevated Temperature: Lomitation by Methionine", Journal of Bacteriology, 107(1)., (1971,), 391-396.

Schanze, K. S, et al., "Functional Polyelectrolytes", in: Langmuir, 2009, vol. 25, (2009), 13698-13702.

Schild, H. G., "Poly(N-Isopropylacrylamide): Experiment, Theory and Application", Prog. Polym. Sci., 17, (1992), 163-249.

Schlüter, A. D., "The Tenth Anniversary of Suzuki Polycondensation (SPC)", Journal of Polymer Science Part A: Polymer Chemistry, 39(10), (2001), 1533-1556.

Senthilkumar, Sadasivam, et al., "Photophysical properties of coumarin-30 dye in aprotic and protic solvents of varying polarities", Photochemistry and Photobiology, 80, (2004), 104-111.

Shi, Songqing, et al., "Synthesis and Characterization of a Water-Soluble Poly(p-phenylenevinylene) Derivative", Macromolecules, 23(8), (1990), 2119-2124.

Stewart, Philip, et al., "Antibiotic resistance of bacteria in biofilms", Lancet, 358., (2001), 135-138.

Stewart, Philip S., et al., "Physiological heterogeneity in biofilms", Nature Reviews Microbiology, 6, (Mar. 2008), 199-210.

Storz, Gisela, et al., "Oxidative stress", Current Opinion in Microbiology, 2., (1999), 188-194.

Stricker, Jesse, et al., "Rapid assembly dynamics of the *Escherichia coli* FtsZ-ring demonstrated by fluorescence recovery after photobleaching", Proc. Nat. Acad. Sci., 99(5)., (2002), 3171-3175.

Tacconelli, Evelina, et al., "Does antibiotic exposure increase the risk of methicillin-resistant *Staphylococcus aureus* (MRSA) isolation? A systematic review and meta-analysis", J. Antimicrob. Chemother.,61(1)., (2008), 26-38.

Tan, C, et al., "Photophysics, aggregation and amplified quenching of a water-soluble poly (phenylene ethynylene)", Chem. Commun., (2002), 446-447.

Tan, C., et al., "Solvent-induced Self-Assembly of a Meta-Linked Conjugated Polyelectrolyte. Helix Formation. Guest Intercalation, and Amplified Quenching", Adv. Mater., vol. 16, No. 14, (2004), 1208-1212.

Tan, Chunyan, et al., "Amplified Quenching of a Conjugated Polyelectrolyte by Cyanine Dyes", J. Am. Chem. Soc., 126, (2004), 13685-13694.

Tan, Chunyan, et al., "Photophysics, aggregation and amplified quenching of a water-soluble poly(phenylene ethynylene)", Chem. Commun., (2002), 446-447.

Tan, Chunyan, et al., "Solvent-Induced Self-Assembly of a Meta-Linked Conjugated Polyelectrolyte. Helix Formation, Guest Intercalation, and Amplified Quenching", Advanced Materials, 16(14), with Supporting Materials, (2004), 1208-1212 (16 pgs.).

Tang, Yanli, et al., "Light-induced antibacterial activity of symmetrical and asymmetrical oligophenylene ethynylenes", Langmuir, 27(8), (2011), 4956-4962.

Tang, Yanli, et al., "Synthesis, Self-Assembly, and Photophysical Behavior of Oligo Phenylene Ethynylenes: From Molecular to Supramolecular Properties", Langmuir, 25(1), (2009), 21-25.

Tang, Yanli, et al., "Synthesis, Self-Assembly, and Photophysical Properties of Cationic Oligo(p-phenyleneethynylene)s", Langmuir, 27(8), (2011), 4945-4955.

Teitzel, Gail, "Heavy Metal Resistance of Bio?lm and Planktonic Pseudomonas aeruginosa", Applied and Environmental Microbiology, 69(4)., (2003), 2313-2320.

Tew, G. N, et al., "", Biochimica et Biophysica Acta 2006, (2006), 1387-1392.

Thomas, III, Samuel W., et al., "Chemical Sensors Based on Amplifying Fluorescent Conjugated Polymers", Chem. Rev., 107, (2007), 1339-1386.

Tiller, J. C., et al., "Designing surfaces that kill bacteria on contact", Proc. Natl. Acad. Sci. USA, 98(11), (May 22, 2001), 5981-5985.

Tong, W., et al., "Single Polyelectrolyte Microcapsules Fabricated by Glutaraldehyde-Mediated Covalent Layer-by-Layer Assembly", Macromol. Rapid Commun., 27, (2006), 2078-2083.

Trauble, Hermann, et al., "The Structure of *Escherichia coli* Membranes Studied by Fluorescence Measurement of Lipid Phase Transitions", Biophys. Acta, 307., (1973), 491-512.

Turro, J, et al., "Luminescent Probes for Detergent Solutions. A Simple Procedure for Determination of the Mean Aggregation Number of Micelles", J. Am. Chem. Soc., 100., (1978), 5951-5952.

Valle, Jaione, et al., "Broad-spectrum biofilm inhibition by a secreted bacterial polysaccharide", Proc. Natl. Acad. Sci. USA, 103(33), (2006), 12558-12563.

Vollmer, Waldemar, et al., "Peptidoglycan structure and architecture", FEMS Microbiol. Rev. 32(2)., (2008), 149-167.

Wallow, Thomas I., et al., "In Aqua Synthesis of Water-Soluble Poly(p-phenylene) Derivatives", J. Am. Chem. Soc., 113, (1991), 7411-7412.

Wang, Deli, et al., "Biosensors from conjugated polyelectrolyte complexes", Proc. Natl. Acad. Sci. USA, 96, (1999), 12287-.

Wang, Deli, et al., "Photoluminescence Quenching of Conjugated Macromolecules by Bipyridinium Derivatives in Aqueous Media: Charge Dependence", Langmuir, 17, (2001), 1262-1266.

Wang, Ying, et al., "Direct Visualization of Bactericidal Action of Cationic Conjugated Polyelectrolytes and Oligomers", Langmuir, 28, (2012), 65-70.

Wang, Ying, et al., "Membrane Perturbation Activity of Cationic Phenylene Ethynylene Oligomers and Polymers", Langmuir Letter, 26(15), (2010), 12509-12514.

Wang, Ying, et al., "Membrane Perturbation Activity of Cationic Phenylene Ethynylene Oligomers and Polymers: Selectivity against Model Bacterial and Mammalian Membranes", Langmuir, 26(15), (Jun. 29, 2010), 12509-12514.

(56) References Cited

OTHER PUBLICATIONS

Wang, Ying, et al., "Understanding the Dark and Light-Enhanced Bactericidal Action of Cationic Conjugated Polyelectrolytes and Oligomers", Langmuir, 29(2)., (2013), 781-792.

Wang, Yingsheng, et al., "Photochemical probes of intramolecular electronc and energy transfer", Chemical Physics, 176, (1993), 305-319.

Wang, Z., et al., "Preparation and application of single polyelectrolyte microcapsules possessing tunable autofluorescent properties.", Colloids and Surfaces A: Physicochemical and Engineering Aspects, 329, (2008), 58-66.

Xu, Shimei, et al., "Effect of the Anionic-Group/Cationic-Group Ratio on the Swelling Behavior and Controlled Release of Agrochemicals of the Amphoteric, Superabsorbent Polymer Poly(acrylic acid-co-diallyldimethylammonium chloride)", Journal of Applied Polymer Science, 102, (2006), 986-991.

Yang, Chaoyong James, et al., "Direct Synthesis of an Oligonucleotide-Poly-(phenylene ethynylene) Conjugate with a Precise One-to-One Molecular Ratio", Angew. Chem. Int. Ed. 44, (2005), 2572-2576.

Zhang, Lian-Hui, et al., "Quorum sensing and signal interference: diverse implications", Molecular Microbiology, 53(6), (2004), 1563-1571.

Zhao, Xiaoyong, et al., "Variable Band Gap Poly(arylene ethynylene) Conjugated Polyelectrolytes", Macromolecules, 39, (2006), 6355-6366.

Zhao, Xiaoyong, et al., "Varible Bsnd Gap Poly(arylene ethynylene) Conjugated Polyelectrolytes", Macromolecules, 39, (2006), 6355-6366.

Zhinjou, Zhou, "Studies of a cyanine-based biosensor and light-induced antibacterial activities of oligophenyleneethynylenes", Dissertation, Chemistry, University of New Mexico, Albuquerque, NM, (Dec. 2010), 165 pgs.

Zhou, Zhijun, et al., "'End-Only' Functionalized Oligo (phenylene ethynylene ) s: Synthesis, Photophysical and Biocidal Activity", J. Phys. Chem. Lett. 1., (2010), 3207-3212.

Zhou, Zhijun, et al., "End-Only" Functionalized Oligo(phenylene ethynylene)s: Synthesis, Photophysical and Biocidal Activity, Journal of Physical Chemistry Letters, 1(21), (2010), 3207-3212.

Zhu, Huiguang, et al., "Synthesis of Size-Controlled Monodisperse Manganese Carbonate Microparticles as Templates for Uniform Polyelectrolyte Microcapsule Formation.", Chem. Mater.,17, (2005), 2323-2328.

"U.S. Appl. No. 13/809,573, Final Office Action dated Dec. 15, 2016", 15 pgs.

"U.S. Appl. No. 13/809,573, Response filed Apr. 17, 2017 to Final Office Acton dated Dec. 15, 2016", 17 pgs.

"U.S. Appl. No. 13/809,573, Non Final Office Action dated Oct. 11, 2017", 12 pgs.

\* cited by examiner

|  | UVA | Dark | UVA | Dark | Dark |
|---|---|---|---|---|---|
|  | OPE | OPE | OPE + TTAB | OPE + TTAB | TTAB NC |
| % Dead | 68.1% | 41.3% | 98.3% | 44.8% | 8.7% |
| % Living | 31.9% | 58.7% | 1.7% | 55.2% | 91.3% |

|  | UVA | Dark | UVA | Dark | Dark |
|---|---|---|---|---|---|
|  | OPE | OPE | OPE + TTAB | OPE + TTAB | TTAB NC |
| % Dead | 74.0% | 72.7% | 99.7% | 97.2% | 56.1% |
| % Living | 26.0% | 27.3% | 0.3% | 2.8% | 43.9% |

CHARGED SINGLET-OXYGEN SENSITIZERS AND OPPOSITELY-CHARGED SURFACTANTS

CROSS-REFERENCE TO RELATED APPLICATIONS

This application claims the benefit of priority of U.S. Provisional Patent Application Ser. Nos. 61/902,057, filed Nov. 8, 2013, and 61/903,811, filed Nov. 13, 2013, the disclosures of which are incorporated by reference herein in their entireties.

STATEMENT OF GOVERNMENT SUPPORT

This invention was made with Government support under grant number HDTRA1-08-1-0053 awarded by the Defense Threat Reduction Agency; and grant number DMR-1207362 awarded by the National Science Foundation. The U.S. Government has certain rights in this invention.

BACKGROUND

The problem of antibiotic-resistant bacteria has become a substantial burden for healthcare providers in the last few decades. Hospitals in the United States have seen a drastic increase in cases of patients acquiring infections of antibiotic-resistant bacteria such as Gram-negative *Klebsiella pneumonia* and *Acinetobacter* baumannii, as well as Gram-positive *Staphylococcus aureus*, to the extent of 1.7 million hospital-acquired infections, annually. See R. M. Klevens, J. R. Edwards, C. L. Richards Jr., T. C. Horan, R. P. Gaynes, D. A Pollock and D. M. Cardo, *Public Health Rep.*, 2007, 122 (2), 160-6. A large number of nosocomial (hospital-acquired) infections are caused by a methicillin-resistant strain of *S. aureus*, which can survive most conventional antibiotic treatments. Several large-scale studies have shown that exposure to antibiotics can increase the chances of acquiring such an infection in a hospital environment, as the antibiotics kill most of the natural flora of the body while allowing the antibiotic-resistant bacteria to thrive. See E. Tacconelli, G. De Angelis, M. A. Cataldo, E. Pozzi and R. Cauda, *J. Antimicrob. Chemother.*, 2008, 61 (1), 26-38; B. S. Cooper, G. F. Medley, S. P. Stone, et al. *Proc. Nat. Acad. Sci.*, 2004, 101 (27), 10223-8; and F. Chamchod and S. Ruan, *Theor Biol Med. Model.* 2012, 9, 25. The development of novel antibiotics or bactericides that do not induce resistance in targeted pathogens is essential for effective treatment of many types of nosocomial infections. See E. K. Nickerson, T. E. West, N. P. Day and S. J. Peacock, *Lancet Infect. Dis.*, 2009, 9, 130-135 and R. Gorwitz, S. K. Fridkin and K. A. Workowski, *Ann. Intern. Med.*, 2008, 148, 310-312.

SUMMARY OF THE INVENTION

The invention is directed, in various embodiments, to compositions including a charged singlet-oxygen sensitizer and an oppositely-charged surfactant. In various embodiments, the charged singlet-oxygen sensitizer is a charged oligo-phenylene ethynylene (OPE) of formula (I)

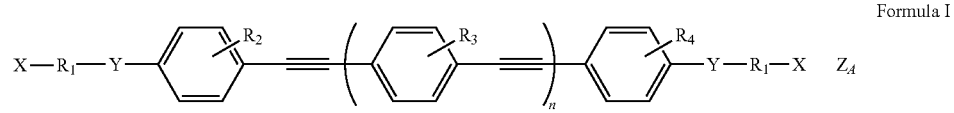

Formula I in which,
both X are a sulfonate group or both X are a quaternary ammonium group;
at each occurrence $R_1$ is independently $(C_1\text{-}C_5)$ alkyl;
each Y is independently O or $CH_2$;
at each occurrence $R_2$, $R_3$, and $R_4$ are independently selected from halogen, $(C_1\text{-}C_6)$alkyl, and $(C_1\text{-}C_6)$alkoxy;
n is about 1 to about 10; and
$Z_A$ signifies two or more charge-balancing counterions.

In various embodiments, the invention relates to a method of enhancing bactericidal properties of a charged oligo-phenylene ethynylene singlet-oxygen sensitizer comprising forming a mixture with an oppositely-charged surfactant.

It has been unexpectedly discovered by the inventors herein that the addition of an oppositely-charged surfactant to an oligo-phenylene ethynylene charged singlet-oxygen sensitizer brings about an unexpected increase in biocidal activity, e.g., versus bacteria in water, in the presence of light and oxygen.

In the case of positively-charged oligo-phenylene ethynylene singlet-oxygen sensitizers, it has been unexpectedly discovered by the inventors herein that addition of a negatively-charged surfactant brings about an increase in biocidal activity. For example, a decrease in the amount of photo-bleaching and loss of biocidal activity is observed when a negatively-charged surfactant is added to a positively-charged singlet-oxygen sensitizer and is contacted with bacteria, in solution, in the presence of oxygen and under illumination by visible or ultraviolet light. Furthermore, addition of the negatively-charged surfactant prolongs the killing of bacteria and the disinfection of objects by the singlet-oxygen sensitizer under illumination in solution when compared to the period of time over which effective biocidal activity is observed in the absence of the negatively-charged surfactant.

In the case of negatively-charged oligo-phenylene ethynylene singlet-oxygen sensitizers it has been unexpectedly discovered by the inventors herein that addition of a positively-charged surfactant to a negatively-charged singlet-oxygen sensitizer brings about an unexpected increase in biocidal activity. Furthermore, it has been discovered that the addition of a positively-charged surfactant allows the negatively-charged singlet-oxygen sensitizer to associate with, and permeate bacterial membranes, resulting in a strong biocidal response when exposed to light.

In addition to enhancing the lifetime of biocides, compositions including a charged singlet-oxygen sensitizer and an oppositely-charged surfactant can be applied to enhance the lifetime of sensors, dyes, and organic LEDs.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
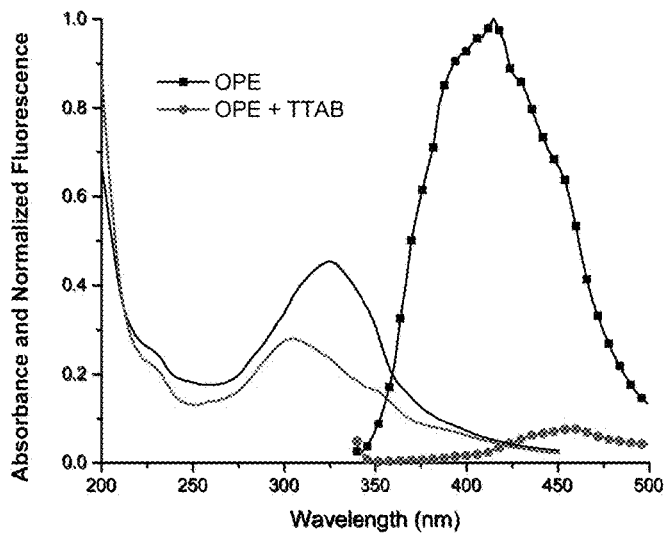
FIG. 1. illustrates UV-Visible absorbance and fluorescence spectra (dotted) for 20 μM OPE alone, and OPE complexed with 80 μM TTAB.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

It has been unexpectedly discovered by the inventors herein that the addition of an oppositely-charged surfactant to an oligo-phenylene ethynylene charged singlet-oxygen sensitizer brings about an unexpected increase in biocidal activity.

In the case of positively-charged (cationic) oligo-phenylene ethynylene singlet-oxygen sensitizers, it has been unexpectedly discovered by the inventors herein that addition of a negatively-charged surfactant brings about an increase in biocidal activity. For example, a decrease in the amount of photo-bleaching and loss of biocidal activity is observed when a negatively-charged surfactant is added to a positively-charged singlet-oxygen sensitizer and is contacted with bacteria, in solution, in the presence of oxygen and under illumination by visible or ultraviolet light. Furthermore, addition of the negatively-charged surfactant prolongs the killing of bacteria and the disinfection of objects by the cationic oligo-phenylene ethynylene singlet-oxygen sensitizer, e.g., OPE 1, see below, under illumination in solution when compared to the period of time over which effective biocidal activity is observed in the absence of the negatively-charged surfactant.

In the case of negatively-charged (anionic) oligo-phenylene ethynylene singlet-oxygen sensitizers, it has been unexpectedly discovered by the inventors herein that addition n of a positively-charged surfactant to a negatively-charged singlet-oxygen sensitizer, e.g., OPE, see below, brings about an unexpected increase in biocidal activity. Furthermore, it has been discovered that the addition of a positively-charged surfactant allows the negatively-charged oligo-phenylene ethynylene singlet-oxygen sensitizer to associate with, and permeate bacterial membranes, resulting in a strong biocidal response when exposed to light.

One aspect of the present invention is based on compositions including a charged singlet-oxygen sensitizer and an oppositely-charged surfactant.

In various embodiments, the charged singlet-oxygen sensitizer is a charged oligo-phenylene ethynylene compound of formula I:

Formula I

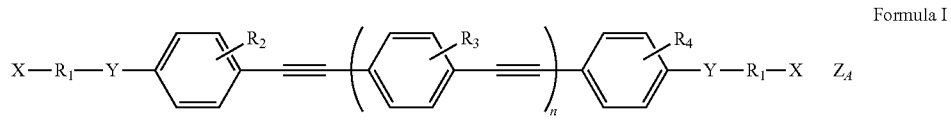

in which,
both X are a sulfonate group or both X are a quaternary ammonium group;
at each occurrence $R_1$ is independently $(C_1$-$C_5)$alkyl;
each Y is independently O or $CH_2$;
at each occurrence $R_2$, $R_3$, and $R_4$ are independently selected from halogen, $(C_1$-$C_6)$alkyl, $(C_1$-$C_6)$alkoxy;
n is 1 to about 10; and
$Z_A$ signifies two or more charge-balancing counterions.

In some embodiments, the variable n can be about 1 to about 8, about 1 to about 6, about 1 to about 4, or 1, 2, 3, 4, 5, 6, 7, 8, 9, or 10.

In some embodiments, compounds useful in the present invention are charged oligo-phenylene-ethynylene compounds of formula II:

Formula II

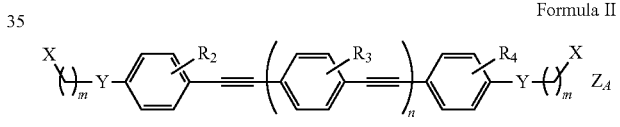

in which,
both X are a sulfonate group or both X are a quaternary ammonium group;
each Y is independently O or $CH_2$;
at each occurrence $R_2$, $R_3$, and $R_4$ are independently selected from halogen, $(C_1$-$C_6)$alkyl, $(C_1$-$C_6)$alkoxy;
m is about 1 to about 5;
n is about 1 to about 10; and
$Z_A$ signifies two or more charge-balancing counterions.

In some embodiments, the variable n can be about 1 to about 8, about 1 to about 6, about 1 to about 4, or 1, 2, 3, 4, 5, 6, 7, 8, 9, or 10.

In some embodiments, compounds useful in the present invention are negatively-charged oligo-phenylene ethynylene compounds of formula III:

Formula III

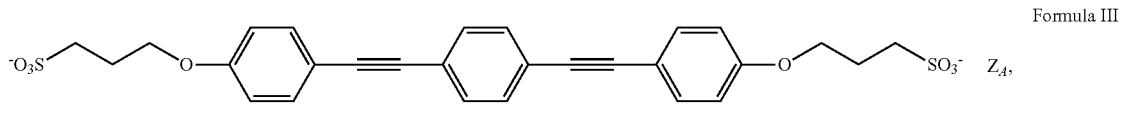

OPE in which, $Z_A$ signifies two charge-balancing counterions.

In some embodiments, compositions useful in the present invention include negatively-charged oligo-phenylene ethynylene compounds of the above formula III, in which the oppositely-charged surfactant includes tetradecyl trimethylammonium bromide (TTAB).

In some embodiments, compounds useful in the present invention are positively-charged oligo-phenylene-ethynylene compounds of formula IV:

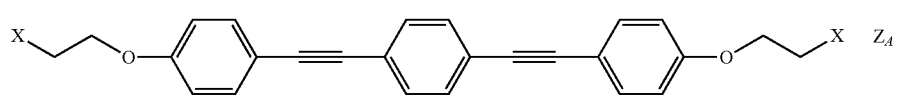

Formula IV in which each X is independently selected from:

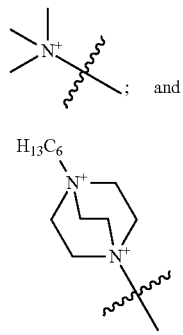

in which, a wavy line indicates a point of bonding; and
in which, $Z_A$ signifies two or more charge-balancing counterions.

In some embodiments, compositions useful in the present invention are positively-charged oligo-phenylene ethynylene compounds of formula V:

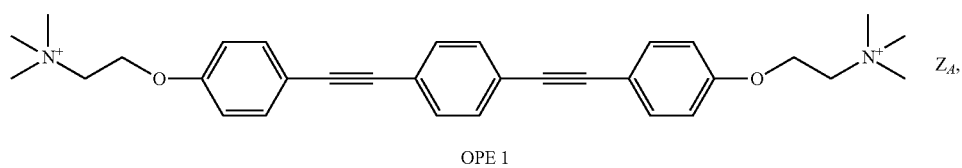

Formula V

OPE 1 in which, $Z_A$ signifies two charge-balancing counterions.

In some embodiments, compositions useful in the present invention are negatively-charged oligo-phenylene-ethynylene compounds of the above formula V, above, wherein the oppositely-charged surfactant includes sodium dodecyl sulfate (SDS).

In various embodiments, the oppositely-charged surfactant is a cationic surfactant.

In some embodiments, cationic surfactants useful in the present invention are $(C_8-C_{20})$alkyl $(C_1-C_4)$trialkyl ammonium quaternary compounds.

In some embodiments, the cationic surfactant is tetradecyl trimethylammonium bromide (TTAB).

In various embodiments, the oppositely-charged surfactant is an anionic surfactant.

In some embodiments, the anionic surfactant is selected from sulfate and sulfonate compounds.

In some embodiments, the anionic surfactant includes sodium dodecylsulfate.

In some embodiments the present invention relates to a method of inactivating a microorganism, which includes contacting the microorganism with an effective amount or concentration of a composition of the present invention.

In various embodiments, the method of inactivating a microorganism, includes the following microorganisms: a bacterium, virus, fungus, mold, slime mold, algae, and yeast.

In various embodiments, the inactivating continues for a longer period of time than does inactivating under comparable conditions but in the absence of the oppositely-charged surfactant.

In various embodiments, the present invention provides for a method of disinfecting an object, including contacting the object with compositions of the present invention.

In some embodiments, the present invention provides for a method of disinfecting an object, including contacting the object with compositions of the present invention, in which the contacting occurs in solution under irradiation by visible light or ultraviolet light.

In various embodiments, the present invention provides for a method of prolonging the period of time over which bacteria are inactivated or objects are disinfected by a singlet-oxygen sensitizer by formulating compositions of the present invention, wherein the composition is irradiated with visible or ultraviolet light in the presence of oxygen.

In various embodiments, the present invention provides for a method of enhancing bactericidal properties of a charged singlet-oxygen sensitizer including forming a mixture with an oppositely-charged surfactant.

In specific embodiments the present invention relates to a method of inactivating a microorganism, which includes contacting the microorganism with an effective amount or concentration of a composition wherein the composition includes compounds of formula I

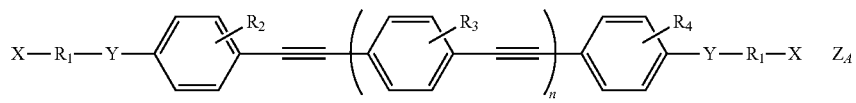

Formula I in which, both X are a sulfonate group or both X are a quaternary ammonium group;

at each occurrence $R_1$ is independently $(C_1-C_5)$alkyl;

each Y is independently O or $CH_2$;

at each occurrence $R_2$, $R_3$, and $R_4$ are independently selected from halogen, $(C_1-C_6)$alkyl, $(C_1-C_6)$alkoxy;

n is about 1 to about 10; and $Z_A$ signifies two or more charge-balancing counterions.

In some embodiments, the variable n can be about 1 to about 8, about 1 to about 6, about 1 to about 4, or 1, 2, 3, 4, 5, 6, 7, 8, 9, or 10.

In various embodiments, the invention provides for a kit for inactivating bacteria or disinfecting objects, the kit including compositions of the present invention, wherein the charged singlet-oxygen sensitizer and oppositely-charged surfactant are in separate sealed containers.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1" is equivalent to "0.0001." All publications, patents, and patent documents referred to in this document are incorporated by reference herein in their entirety, as though individually incorporated by reference.

The term "about" as used herein can allow for a degree of variability in a value or range, for example, within 10%, within 5%, or within 1% of a stated value or of a stated limit of a range.

The term "charged singlet-oxygen sensitizer," as used herein refers to oligo-phenylene ethynylene (OPE) compounds capable of generating singlet-oxygen in solution, in the presence of oxygen and light, wherein the compounds have a net negative or net positive electrical charge. Non-limiting examples include the OPE and OPE 1 compounds discussed herein. Further, the term "charged singlet-oxygen sensitizer" also encompasses charged singlet-oxygen generators.

The term "counterion," and grammatical equivalents refers to negatively charged species or positively charged species that bear the opposite electrical charge relative to the charged molecule under discussion. Non-limiting examples of negatively charged species include species such as chloride, bromide, hydroxide, acetate, and sulfate. Non-limiting examples of positively charged species include species such as The term "anionic surfactant" refers to a surfactant with a net negative electrical charge. Non-limiting examples of suitable anionic surfactants include sodium dodecyl sulfate (SDS) and 1,2-Dioleoyl-sn-glycero-3-phospho-rac-(1-glycerol) ("DOPG").

The term "cationic surfactant" refers to a surfactant with a net positive electrical charge. Non-limiting examples of suitable cationic surfactants include tetradecyltrimethylammonium bromide (TTAB) and 1,2-dioleoyl-3-trimethylammonium-propane ("DOTAP").

A "biocidal" substance, as the term is used herein, refers to a substance that under defined conditions can kill microorganisms, inhibit the growth of individual microorganisms and populations of microorganisms, prevent the establishment of microbial populations, and the like.

The term "inactivate," and grammatical equivalents, means killing, eliminating, neutralizing, or reducing the capacity of a pathogenic microorganism to infect a host on contact.

The term "disinfecting," and grammatical equivalents, refers to the process of destruction of or prevention of the growth of biological contaminants.

The terms "enhance" or "enhancing" refers, for example, to increasing or prolonging either in potency or duration a desired effect.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be hydrogen (in examples that include other carbon atoms) or a carbon-based moiety, and wherein the carbon-based moiety can itself be further substituted.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O) R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O) OR, N(R)C(O)R, N(R)C(S)R, N(R)C(O)N(R)$_2$, N(R)C(S)N (R)$_2$, N(COR)COR, N(OR)R, C(=NH)N(R)$_2$, C(O)N(OR) R, or C(=NOR)R, wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted with J; or wherein two R groups bonded to a nitrogen atom or to adjacent nitrogen atoms can together with the nitrogen atom or atoms form a heterocyclyl, which can be mono- or independently multi-substituted with J.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH (CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The terms "halo," "halogen," or "halide" group, as used herein, by themselves or as part of another substituent, mean, unless otherwise stated, a fluorine, chlorine, bromine, or iodine atom.

The term "radiation" as used herein refers to energetic photons travelling through a medium or space. Examples of radiation are visible light and ultraviolet (UV) light.

The term "singlet oxygen", "singlet-oxygen" and "$^1O_2$," refers to the first electronically excited state of molecular oxygen. Molecular oxygen is a ground state triplet.

The term "UVA" refers to ultraviolet A, electromagnetic radiation in and near wavelengths of about 320 to about 400 nm.

The term "irradiation" refers to the exposure of a sample of interest to radiation.

The term "light" as used herein refers to electromagnetic radiation in and near wavelengths visible by the human eye, and includes ultra-violet (UV) light.

The term "UV light" as used herein refers to ultraviolet light, which is electromagnetic radiation with a wavelength of about 10 nm to about 400 nm.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof.

The term "solvent" as used herein refers to a liquid that can dissolve a solid, liquid, or gas. Nonlimiting examples of solvents are silicones, organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "air" as used herein refers to a mixture of gases with a composition approximately identical to the native composition of gases taken from the atmosphere, generally at ground level. In some examples, air is taken from the ambient surroundings.

The term "room temperature" as used herein refers to a temperature of about 15° C. to 28° C.

The term "standard temperature and pressure" as used herein refers to 20° C. and 101 kPa.

EXAMPLES

Various embodiments of the present invention can be better understood by reference to the following Examples which are offered by way of illustration. The present invention is no limited to the Examples given herein.

Example 1

Solid OPE was synthesized according to Zhou, Z.; Corbitt, T. S.; Parthasarathy, A.; Tang, Y.; Ista, L. K.; Schanze, K. S.; Whitten, D. G. "End-Only" Functionalized Oligo (phenylene ethynylene)s: Synthesis, Photophysical and Biocidal Activity. *J. Phys. Chem. Lett.* 2010, 1, 3207-3212.

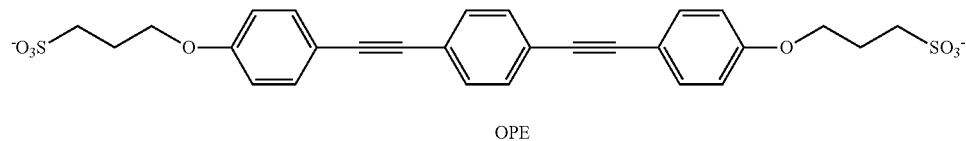

OPE

This OPE, as a sodium salt, was dissolved in filtered water with a resistivity of 18 MΩ*cm to a final concentration of 20 μM. Tetramethyl trimethylammonium Bromide (TTAB) was purchased from Sigma-Aldrich (St. Louis, Mo.), and dissolved in filtered water with a resistivity of 18 MΩ*cm to a final concentration of 80 μM. A solution of 20 μM OPE and 80 μM TTAB was prepared in a quartz cuvette, and UV-visible absorption and fluorescence spectroscopy were performed with a Molecular Devices Spectramax M5 spectrophotometer (Molecular Devices, Sunnyvale, Calif.). These are shown in FIG. 1.

All media and buffers were prepared with deionized water with a resistivity of at least 18 MΩ cm. Nutrient broth 234000 (Difco) was prepared according to manufacturer's instructions. Nutrient agar was prepared upon the addition of 8 g/L bacto agar (Difco). *Staphylococcus aureus* (ATCC 10832) and *Escherichia coli* (ATCC 29425) were both grown from glycerol-preserved stock which originated from first-generation cultures of original ATCC lyophilates grown in nutrient broth (containing 20% glycerol) and subsequently stored at −70° C. Cells of the aforementioned strains were grown upon the inoculation of glycerol stock on Difco nutrient agar at 37° C. for 24 hours. Cell culture preparation for biocidal testing entailed scraping *S. aureus* or *E. coli* colonies off their agar plates and transferring them to nutrient broth for growth. Cells were then incubated in an Orbital Incubator Shaker (American Instruments, Lafayette, Calif.) for 18 h at 37° C. with rapid shaking (250 rpm). Following the incubation period, cells were washed by two 15 min centrifugations at 4,400 rpm; in each case, supernatant was replaced by 30 mL of 0.85% NaCl following pellet formation.

The bacterial stock solution was either diluted or concentrated to $2\times10^7$ cells/mL. Samples were diluted by the addition of 0.85% NaCl, while concentrating the sample entailed centrifugation to pellet the cells, followed by removal of the necessary amount of supernatant and subsequent resuspension of the pellet by vortexing. 500 μL of bacterial solution was added to glass vials with 500 μL of sample solution to reach a final volume of 1 mL prior to analysis. Samples tested contained 10 μM OPE, 40 μM TTAB, or both 10 μM OPE and 40 μM TTAB. Biocidal activity under UVA irradiation was determined using a Luzchem LZC-ORG photoreactor (Luzchem Research, Ontario, Canada). This photoreactor was configured with 10 UVA lamps (0.975 mW/cm$^2$ over 316-400 nm) with a fan-powered exhaust to keep a stable temperature of 28° C. and a rotating carousel for homogeneous irradiation of samples. Samples exposed in the dark were kept at room temperature, 25° C. 70% Ethanol was used as a positive control, and a 60 minute UVA-irradiated sample of bacteria was used as a negative control.

Figure 2:
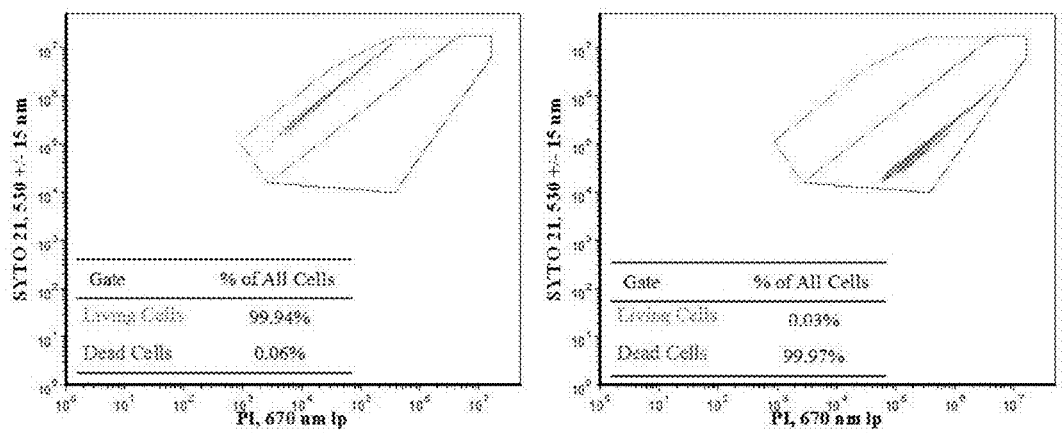
FIG. 2. illustrates a flow cytometry gating scheme used for biocidal analysis of *S. aureus*, with a dark negative control in the left panel and a 70% EtOH positive control in the right panel.
Figure 3:
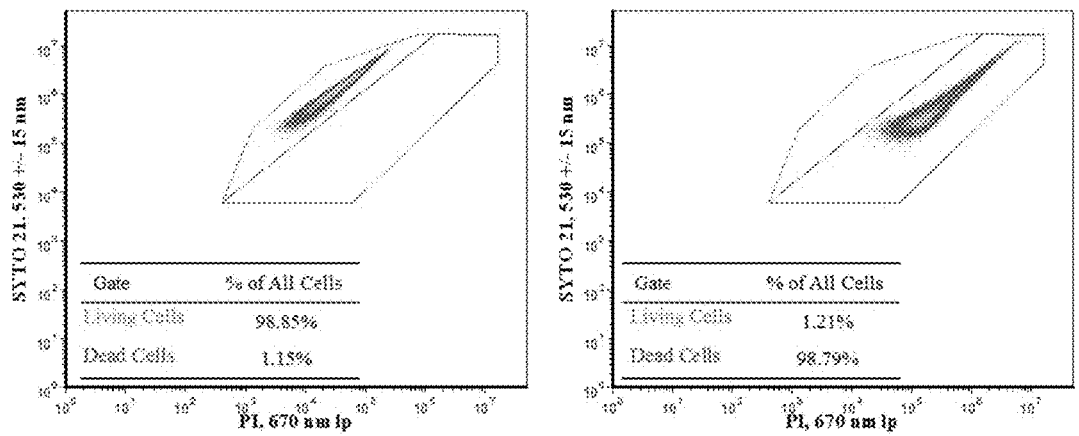
FIG. 3. illustrates a flow cytometry gating scheme used for biocidal analysis of *E. coli*, with a dark negative control in the left panel and a 70% EtOH positive control in the right panel.

Flow cytometry gating and analysis were carried out as performed in previous studies of biocidal activity of OPEs (see Z. Malik, J. Hanania, Y. Nitzan New trends in photobiology bactericidal effects of photoactivated porphyrins—An alternative approach to antimicrobial drugs, *Journal of Photochemistry and Photobiology B: Biology* 1990, 5 (3-4), 281-293). Flow cytometry was utilized to determine the cell concentration of *S. aureus* or *E. coli* in the 0.85% NaCl-suspended bacterial stock solutions. The Accuri C6 (Becton Dickinson, Franklin Lakes, N.J.) used was equipped with a blue laser that excites at 488 nm, as well as two filters: a green fluorescence filter (FL-1: 530 nm) and a red fluorescence filter (FL-3: 670 nm long-pass). A primary threshold ensured that only events exhibiting 40,000 FSC-A scatter units were included in the data, while a secondary threshold ensured that only events exhibiting 250 FL-1 fluorescence units (live stain fluorescence channel) were included. The core size of the flow cytometer was set to 10 μm, with a flow rate of 14 μL/min. 100,000 events were recorded in each sample. Cells were stained with 5 mM SYTO 21 (live stain; Life Technologies, Grand Island, N.Y.) and 1.5 mM propidium iodide (dead stain; Life Technologies, Grand Island, N.Y.) for 15 min prior to flow cytometry analysis. Flow cytometry gating schemes are shown for *S. aureus* and *E. coli* in FIGS. 2 and 3 of the supporting information, respectively.

The results of the live/dead assay were verified by confocal fluorescence microscopy using a Zeiss Confocal microscope with an Ar laser (488 nm) and a HeNe laser (513 nm) as excitation sources. Standard plating techniques were utilized to validate flow cytometry data. This entailed pipetting and spreading 50 μL aliquots of diluted, unstained sample, onto nutrient agar plates. The plates were incubated at 37° C. for 18 hours, colonies were counted, and viabilities were calculated relative to the UVA negative control. All exposure times for OPE with bacteria in light or dark were 60 minutes in duration.

Figure 4:
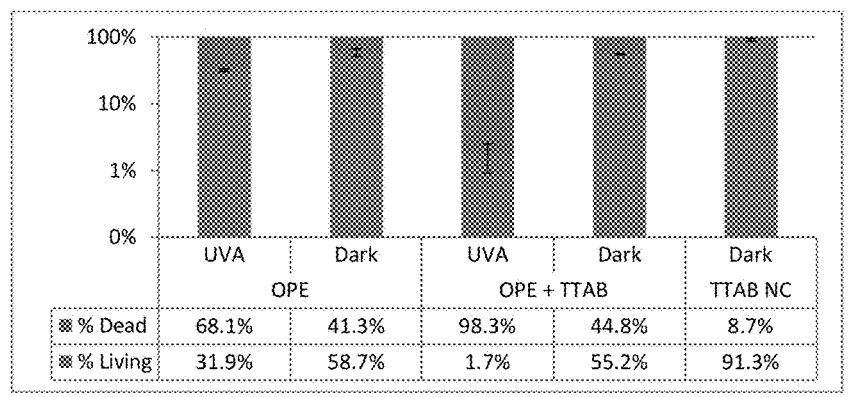
FIG. 4. illustrates viability of *S. aureus* in logarithmic scale after one hour of exposure to OPE, TTAB, or the OPE-TTAB complex. Viability is calculated relative to that of a negative control exposed to UVA light for 1 hour.
Figure 5:
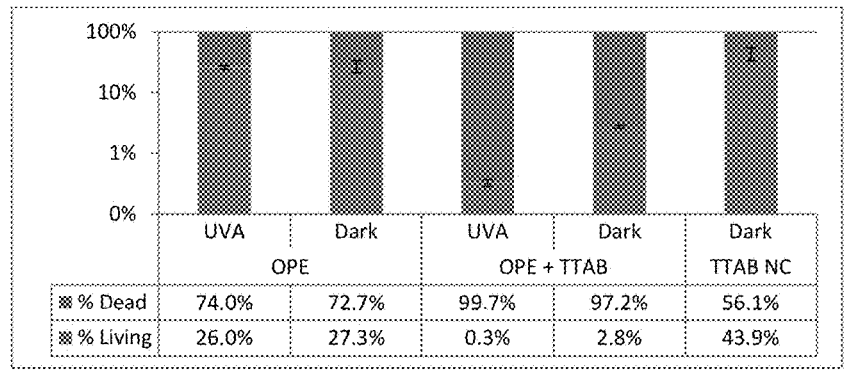
FIG. 5. illustrates viability of *E. coli* in logarithmic scale after one hour of exposure to OPE, TTAB, or the OPE-TTAB complex. Viability is calculated relative to that of a negative control exposed to UVA light for 1 hour FIG. 6. illustrates biocidal activity of OPE and the OPE-TTAB complex against Gram-positive *S. aureus* after 1 hour of exposure in the light or dark.
Figure 6:
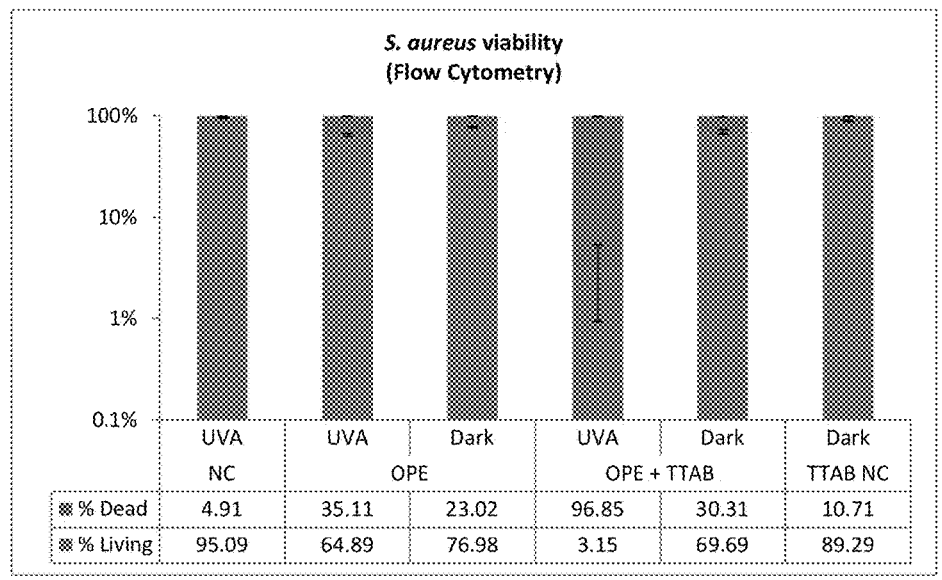
Figure 7:
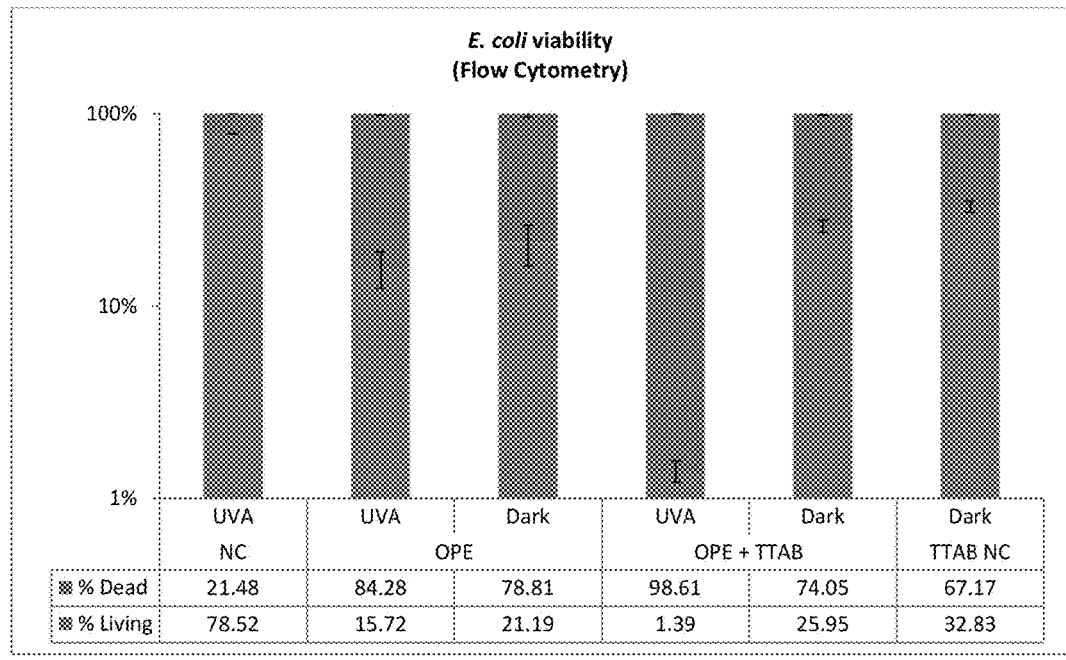
FIG. 7. illustrates biocidal activity of OPE and the OPE-TTAB complex against Gram-negative *E. coli* after 1 hour of exposure in the light or dark.
Figure 8:
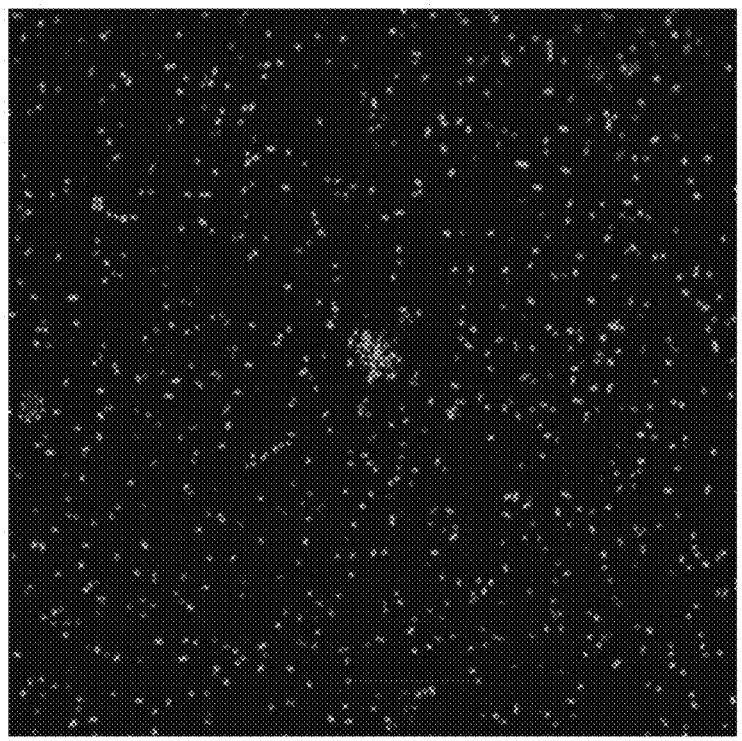
FIG. 8. illustrates a confocal fluorescence microscope image of the negative control of *E. coli* after 1 hour of UVA irradiation. The "live" stain is SYTO9 in green, and the "dead" stain is propidium iodide in red. The scale bar indicates 20 μm.
Figure 9:
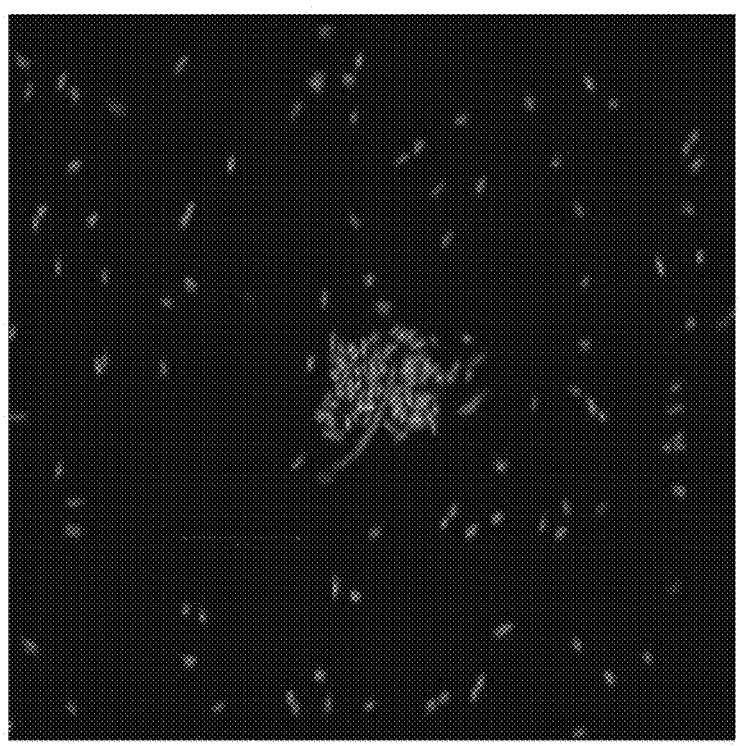
FIG. 9. illustrates a confocal fluorescence microscope image of *E. coli* exposed to the OPE-TTAB complex in the light for an hour. The "live" stain is SYTO9 in green, and the "dead" stain is propidium iodide in red. The scale bar indicates 10 μm.
Figure 10:
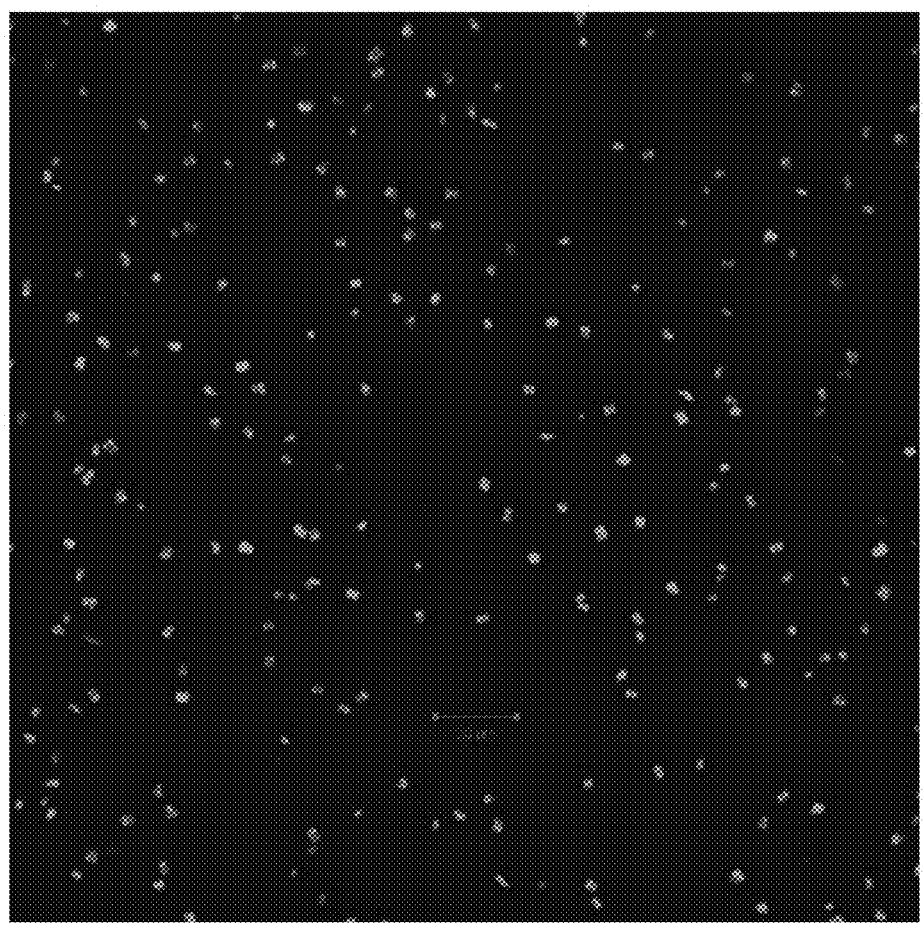
FIG. 10. illustrates a confocal fluorescence microscope image of the negative control of *S. aureus*. The "live" stain is SYTO9 in green, and the "dead" stain is propidium iodide in red. The scale bar indicates 20 μm.
Figure 11:
FIG. 11. illustrates a confocal fluorescence microscope image of *S. aureus* exposed to 40 μM TTAB in the light for an hour. The "live" stain is SYTO9 in green, and the "dead" stain is propidium iodide in red. The scale bar indicates 20 μm.
Figure 12:
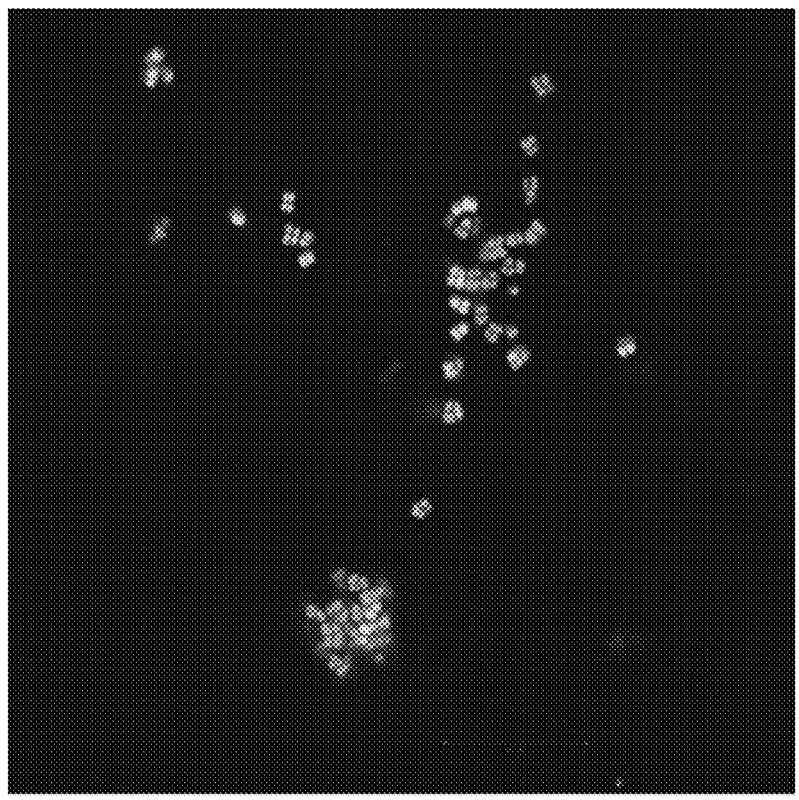
FIG. 12. illustrates a confocal fluorescence microscope image of *S. aureus* exposed to the OPE-TTAB complex in the light for an hour. The "live" stain is SYTO9 in green, and the "dead" stain is propidium iodide in red. The scale bar indicates 20 μm.

The results of biocidal testing using standard plating techniques are shown for *S. aureus* and *E. coli*, in FIGS. 4 and 5, respectively. Flow cytometry results were obtained as support for the plating and are shown in FIGS. 6 and 7 for *S. aureus* and *E. coli*, respectively. In addition, confocal fluorescence microscopy was used to visualize and verify the biocidal measurements, and images are shown in FIGS. 8-12.

The OPE to TTAB ration was kept at a 1:4 ratio so that complex formation is assured and the concentration of TTAB (40 µM) is mostly non-biocidal. This concentration is far below the reported values (5 mM) for the minimum inhibitory concentration of TTAB against both S. aureus and E. coli. See S. Buffet-Bataillon, P. Tattevin, M. Bonnaure-Mallet, A. Jolivet-Gougeon, Emergence of resistance to antibacterial agents: the role of quaternary ammonium compounds—a critical review, *International Journal of Antimicrobial Agents* 2012, 39 (5), 381-389). In FIG. 4 it is shown that only 8.7% of Gram-positive S. aureus was killed by TTAB alone. Higher killing is observed with E. coli (FIG. 5, 56.1%) than with S. aureus. This differences between killing of Gram-positive and Gram-negative bacteria by surfactant has been observed previously with SDS. See E. H. Hill, H. C. Pappas, D. G. Evans, and D. G. Whitten. Cationic oligo-phenylene ethynylenes form complexes with surfactants for long-term light-activated biocidal applications *Photochem. Photobiol. Sci.* 2014, 13, 247-253. See E. H. Hill, H. C. Pappas, D. G. Evans, and D. G. Whitten Cationic oligo-phenylene ethynylenes form complexes with surfactants for long-term light-activated biocidal applications *Photochem. Photobiol. Sci.* 2014, 13, 247-253. As the concentration of TTAB used (40 µM) is far below the critical micelle concentration (4.3 mM), the biocidal activity is relatively low and allows study of the effect of complexation of oligo-phenylene ethynylenes without a significant bias due to killing by TTAB. See D. F. Evans, M. Allen, B. W. Ninham, A. Fouda, Critical Micelle Concentrations for Alkyltrimethylammonium Bromides in Water from 25 to 160 C. *J. Solution Chem.* 1984, 13, 87.

OPE alone did exhibit modest biocidal activity against both strains of bacteria in both light and dark. As shown in FIG. 4, 10 µM OPE killed 68.1% of S. aureus in the light and 41.3% in the dark. It is worth noting that immediate killing observed by flow cytometry showed lower killing than standard plating techniques, with 35.1% killed under UVA irradiation and 23.2% in the dark. It is reasonable that the biocidal activity of this compound is low, as this has been previously shown for oligo-phenylene ethynylenes. See Zhou, Z.; Corbitt, T. S.; Parthasarathy, A.; Tang, Y.; Ista, L. K.; Schanze, K. S.; Whitten, D. G. "End-Only" Functionalized Oligo(phenylene ethynylene)s: Synthesis, Photophysical and Biocidal Activity. *J. Phys. Chem. Lett.* 2010, 1, 3207-3212. It has been also shown with in vitro studies of model membranes that the anionic biocides do not affect the integrity of the membrane. See Wang Y.; Tang Y.; Zhou Z.; Ji E.; Lopez G. P.; Chi E. Y.; Schanze K. S.; Whitten D. G. Membrane Perturbation Activity of Cationic Phenylene Ethynylene Oligomers and Polymers: Selectivity against Model Bacterial and Mammalian Membranes. *Langmuir* 2010, 26, 12509-12514. This is likely the result of unfavorable electrostatic interactions between the OPE and the net-anionic bacterial membrane, which can result in the repulsion of the oligo-phenylene ethynylene sulfonates from the negatively-charged lipids.

The complex between the OPE and TTAB showed significant enhancement of biocidal activity under UVA irradiation compared to either OPE or TTAB alone. As shown in FIG. 4, 98.3% of S. aureus were killed by the OPE-TTAB complex in the light. The killing in the dark was significantly lower (44.8%), with little change from the dark killing observed with the OPE alone. Against Gram-negative E. coli, the complexation with TTAB resulted in significant enhancement of both light and dark killing, as shown in FIG. 5. Under UVA irradiation, the OPE-TTAB complex resulted in a 3 log reduction of bacteria, with 99.7% dead. Even in the dark, significant enhancement was observed, with 97.2% of E. coli killed by the OPE-TTAB complex. The concentration of 10 µM OPE is reduced by a factor of 10 to 100 compared to the concentrations that have been reported for 4-6 log killing for this class of compounds, and these levels can easily be reached with an increase of the OPE concentration.

These results suggest that the surfactant enhances the ability of the OPE to associate with the cell membrane, particularly in the case of Gram-negative E. coli. Since the primary mechanism of light-induced biocidal activity is singlet-oxygen generation leading to reactive oxygen species (ROS), and singlet-oxygen has a very short lifetime in water, close proximity to the cell is essential. See B. A. Lindig, M. A. J. Rodgers, A. P. Schaap Determination of the lifetime of singlet-oxygen in water-d2 using 9,10-anthracenedipropionic acid, a water-soluble probe *J. Am. Chem. Soc.* 1980, 102 (17), 5590-5593. Bacterial cell membranes are net-anionic, and it is likely that the reason the anionic compound is not an effective biocide is that it cannot get close enough to affect the cell membrane with ROS. See Neuhaus, F. C., & Baddiley, J. A continuum of anionic charge: structures and functions of D-alanyl-teichoic acids in gram-positive bacteria. *Microbiology and Molecular Biology Reviews* 2003, 67 (4), 686-723; Nikaido H. Outer membrane. In: Neidhardt F C, Curtiss III R, Ingraham J L, Lin E C C, Low K B Jr, Magasanik B, Reznikoff W S, Riley M, Schaechter M, Umbarger H E, editors. *Escherichia coli and Salmonella*: cellular and molecular biology. 2nd ed. Washington, D.C: American Society for Microbiology; 1996. pp. 29-47; and Träuble H., Overath P. The structure of *Escherichia coli* membranes studied by fluorescence measurements of lipid phase transition. *Biochim. Biophys. Acta* 1973, 307, 491-512. Based on the results disclosed herein, one can predict that a layer of cationic surfactant surrounding the OPE provides the electrostatic attraction needed to bring the complex into close proximity of the membrane. The increased killing of E. coli (56%) by the TTAB alone compared to S. aureus (9%) suggests that the interactions between TTAB and the Gram-negative bacterial membranes are greater. In addition, the dark biocidal activity of the OPE-TTAB complex was enhanced with E. coli but not with S. aureus. This is reasonable, as the structure of the Gram-positive cell wall is more complex, and the thick peptidoglycan outer layer may serve as a greater barrier to entry to the plasma membrane. See Vollmer, W., Blanot, D., & De Pedro, M. A. Peptidoglycan structure and architecture. *FEMS Microbiol. Rev.* 2008, 32 (2), 149-167. The outer membrane of the Gram-negative cell wall is known to contain negatively-charged lipids such as glycerophospholipids, and these would readily associate with the quaternary ammonium headgroup of TTAB. In addition, it is likely that the TTAB is involved in a cation exchange process with the lipids in the Gram-negative bacterial membrane. This suggests that the enhancement of biocidal activity observed is the result of increased interactions between the OPE and the membrane due to the cationic TTAB layer.

While close proximity is enough to significantly enhance biocidal activity in the light, there can be additional mechanisms for the biocidal enhancement in both light and dark. In-vitro studies of bacterial membrane mimics also show that the oligo-phenylene ethynylenes do not induce membrane damage. The structure of the OPE-TTAB complex can consists of the aliphatic backbone of several TTAB molecules solvating the backbone of the OPE, while the quaternary ammoniums of the TTAB are associated with the sulfonate groups of the OPE. With this structure, the TTAB molecules can associate on the periphery of the complex without electrostatic association with the OPE sulfonates, due to favorable hydrophobic interactions between the hydrocarbon tails of the TTAB. This net-cationic complex can strongly interact with the net-negative bacterial membrane.

Figure 13:
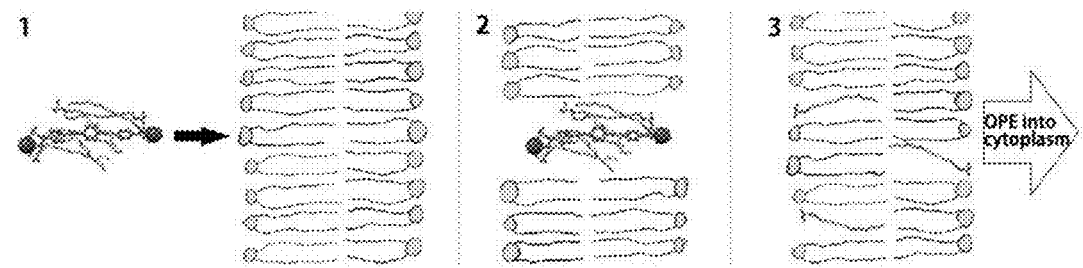
FIG. 13. illustrates a schematic of the proposed mechanism behind enhancement of light-activated biocidal enhancement. 1: The OPE-TTAB complex is formed and added to the bilayer (lipids shown with yellow headgroups). 2: The OPE-TTAB complex, with net-positive charge, intercalates with the anionic lipid bilayer. 3: The TTAB from the complex dissociates into the bilayer and associates with anionic lipids; this results in repulsive electrostatic force between the OPE and the bilayer, ejecting it from the membrane into either the periplasmic space (for Gram-negative bacterial outer membranes) or the cytoplasm.

Following incorporation of the OPE-TTAB complex into the membrane, TTAB can "dissolve" into the fluid environment of lipids in the membrane. Once disassociated from its "shield" of TTAB, the OPEs can repel the negative lipids in the membrane. There are two mechanisms by which this can enhance biocidal activity. First, the repulsion of lipids in the membrane can cause instabilities that lead to membrane disruption or leakage, ultimately causing cell death. As the OPE is repelled, it can be ejected from the membrane into the cytoplasm or periplasm, where it can then be able to easily damage cytoplasmic contents with ROS when irradiated. This mechanism of enhanced biocidal activity is shown in the schematic in FIG. 13.

Example 2

The synthesis of OPE 1 has been reported in the literature. See Y. Wang, S. D. Jett, J. Crum, K. S. Schanze, E. Y. Chi and D. G. Whitten, *Langmuir*, 2013, 29 (2), 781-92. OPE 1 was mixed with sodium dodecylsulfate (SDS).

scatter units or greater were included in the data. The secondary threshold was utilized to remove events exhibiting less than 250 FL-1 fluorescence units (live stain fluorescence channel) from the data. Flow cytometer core size in all experiments was 10 µm, with a flow rate of 14 µL/minute. Using these settings, 20 µL of un-stained stock solution was sufficient for identifying the stock concentration of cells.

For biocidal testing, the stock solution was either diluted or concentrated to $2 \times 10^7$ cells/mL. Equal volumes of the sample and bacterial solution were added to glass tubes prior to analysis. Cells were stained with 5 mM SYTO 21 (live stain; Life Technologies, Grand Island, N.Y.) and 1.5 mM Propidium iodide (dead stain; Life Technologies, Grand Island, N.Y.) for 15-30 minutes prior to flow cytometry anaylsis. An example of the flow cytometry gating scheme for *E. coli* is shown below, in FIG. 14. The UVA-irradiated negative control is shown on the left side of the figure, and the Ethanol positive control is shown on the right.

The solid compound OPE 1, as a dichloride salt, was dissolved in filtered water with a resistivity of 18 MΩ*cm to a final concentration of 10 µM. The solution was then exposed to UVA radiation via a Luzchem LZC-ORG photoreactor (Luzchem Research, Ontario, Canada) in a quartz tube or cuvette. This photoreactor was configured with 10 LZC-UVA lamps (>5.3 mW-cm$^{-2}$ over 316-400 nm,

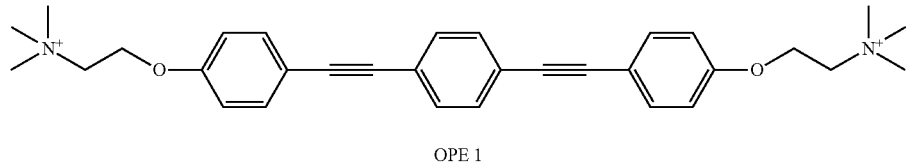

OPE 1

All media and buffers were prepared using deionized water with a resistivity exceeding 18 MΩ*cm. Nutrient Broth 234000 (Difco) was prepared according to manufacturer's instructions, and Nutrient Agar was prepared upon the addition of 8 g/L Bacto agar (Difco). Both *S. aureus* (ATCC 25923) and *E. coli* (ATCC 29425) were grown from glycerol-preserved stock. The frozen stock aliquots were generated from first-generation cultures of the original ATCC lyophilate, which were grown in Nutrient Broth containing 20% glycerol, and subsequently stored at −70° C. The cells were grown by inoculating the glycerol stock on Difco Nutrient Agar for 24 hours at 37° Celsius. For biocidal testing, *S. aureus* and *E. coli* cells were scraped off the agar plate with a flame-sterilized wire and transferred to nutrient broth. Cells were incubated in an Orbital Incubator Shaker (American Instruments, Lafayette, Calif.) at 37° Celsius in nutrient broth with rapid shaking (250 rpm) for 18 hours. Following the 18-hour incubation period, cells were separated from the nutrient broth by two 15-minute centrifugations at 4,400 rpm, each of which was followed by removal of the supernatant and re-suspension in 30 mL 0.85% NaCl.

Flow cytometry was implemented to determine the cell concentration of the 0.85% NaCl-suspended bacterial stock solutions. An Accuri C6 flow cytometer (Becton Dickinson, Franklin Lakes, N.J.) equipped with a blue laser that excites at 488 nm was utilized. Two filters were used: a green fluorescence filter (FL-1: 530 nm) and a red fluorescence filter (FL-3: 670 nm long pass). Two thresholds were used, a primary threshold and a secondary threshold. The primary threshold ensured that only events exhibiting 40,000 FSC-A Luzchem Research, Ontario, Canada) with a fan-powered exhaust to keep a stable temperature and a carousel for homogeneous irradiation of samples. Progress of the photolysis was monitored by UV-visible absorption spectroscopy with a Molecular Devices Spectramax M5 spectrophotometer (Molecular Devices, Sunnyvale, Calif.). Sodium dodecyl sulfate (SDS) was obtained from Sigma Aldrich. For the OPE 1-SDS complexes, 10 µM OPE 1 was mixed with 40 µM SDS, 0.24% of the critical micelle concentration (CMC). *S. aureus* samples were exposed to a OPE 1-SDS complex where the concentration of SDS was 0.33 mM, as they were much more resilient to killing caused by SDS. Samples were irradiated for 0, 30, 60, and 120 minutes prior to exposure to bacteria. Once exposed to OPE 1 or 1-SDS complex, *E. coli* and *S. aureus* samples were irradiated with UVA in the photoreactor for 30 minutes and 15 minutes, respectively.

An example of the flow cytometry gating scheme for *S. Aureus* is shown below, in FIG. 15. The UVA-irradiated negative control is shown on the left side of the figure, and the Ethanol positive control is shown on the right.

Figure 16:
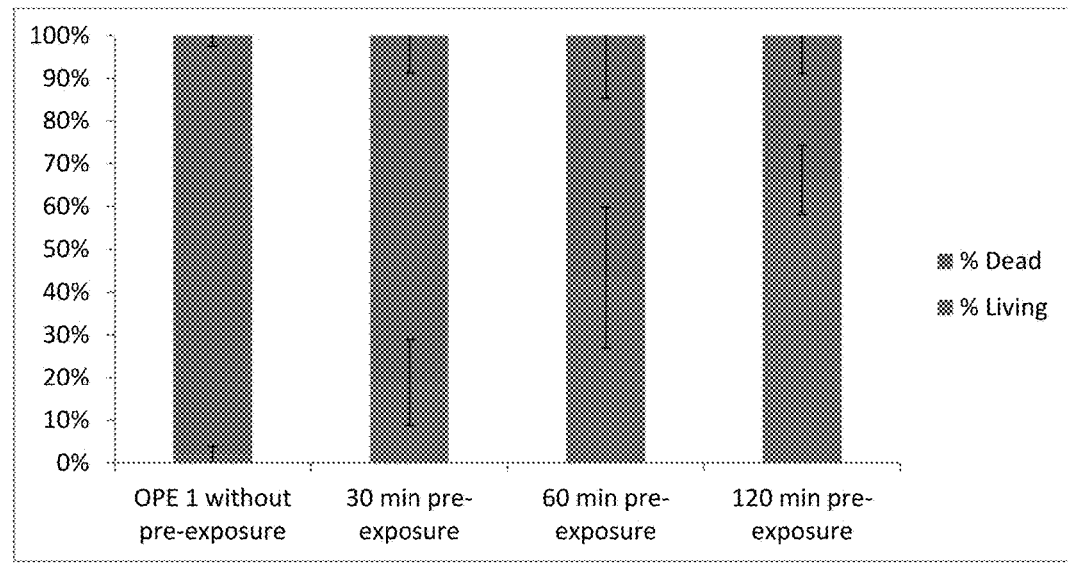
FIG. 16. illustrates biocidal activity of OPE 1 vs. *E. Coli* with samples irradiated for 0, 30, 60, or 120 minutes prior to bacterial exposure.
Figure 17:
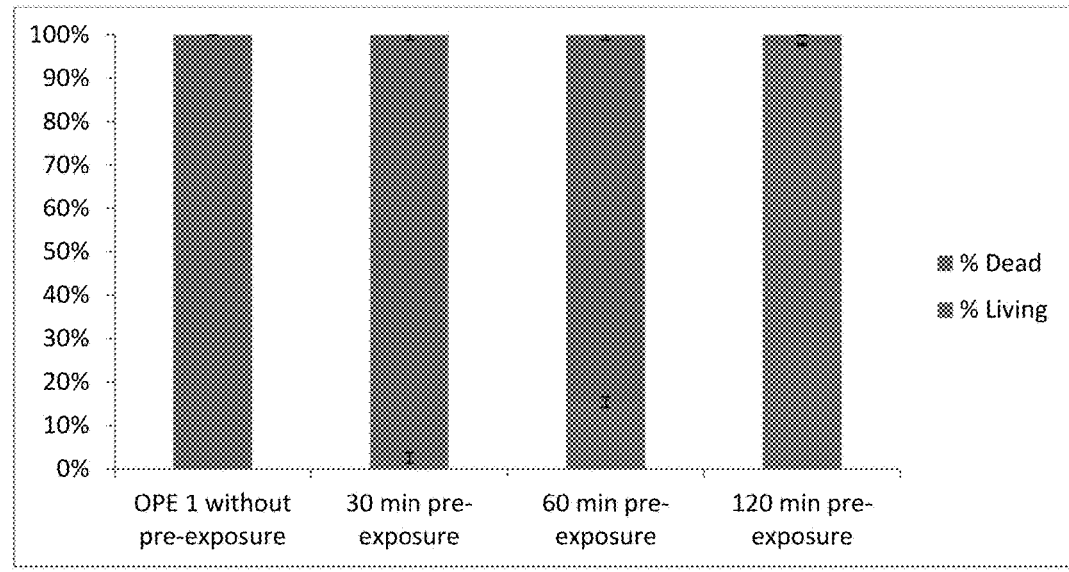
FIG. 17. illustrates biocidal activity of OPE 1 vs. *S. Aureus* with samples irradiated for 0, 30, 60, or 120 minutes prior to bacterial exposure.

The bacterial killing of *E. coli* by OPE 1 as a function of pre-irradiation time is shown below in FIG. 16, and the killing of *S. aureus* is shown in FIG. 17.

Figure 14:
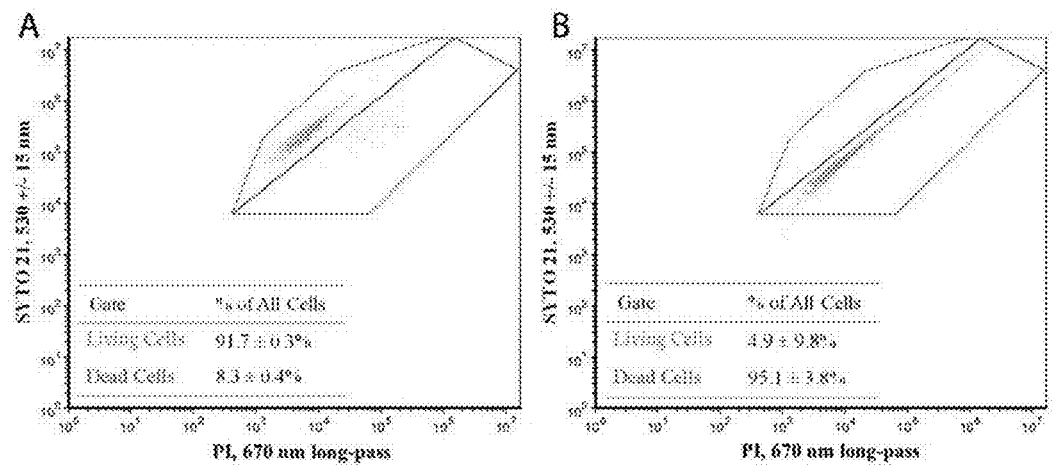
FIG. 14. illustrates a flow cytometry gating for *E. coli*; A. UVA—irradiated negative control; B. 70% Ethanol positive control.
Figure 15:
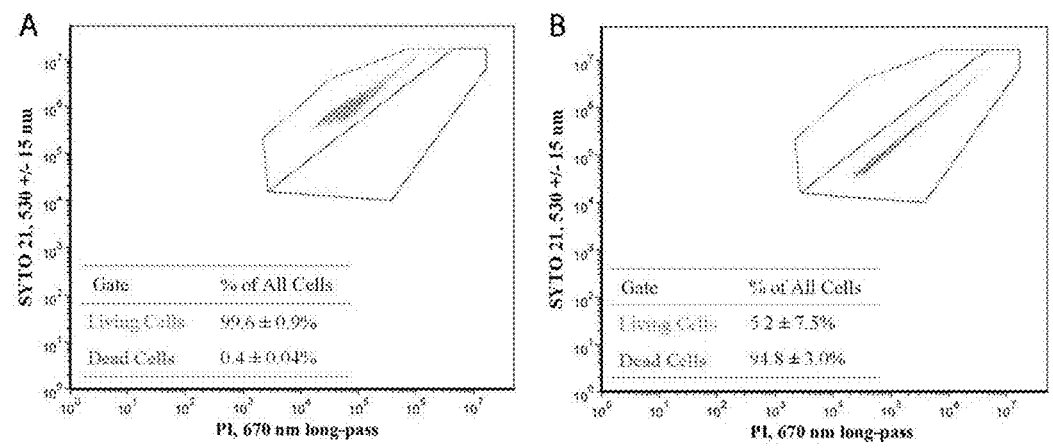
FIG. 15. illustrates a flow cytometry gating for *S. Aureus*; A. UVA—irradiated negative control; B. 70% Ethanol positive control.

The results of the live/dead assay carried out using flow cytometry reveal a significant drop in biocidal activity of OPE 1, even after only 30 minutes of UVA irradiation prior to bacterial exposure. While this drop in biocidal activity is significant, there is a much quicker decrease in absorbance and fluorescence upon irradiation. It was reported that within 2 minutes of photolysis under the same conditions, the absorbance of the compound was observed to diminish and the fluorescence was completely quenched. See E. H. Hill, D. G. Evans and D. G. Whitten, *Langmuir,* 2013, 29 (31), 9712-20. However, as shown in FIGS. 14 and 15, there was still some biocidal activity at 30 minutes and beyond. This suggests that the initial photoproducts can still be biocidal, and can continue to function for a time, albeit less efficiently. However, by 2 hours of pre-exposure the biocidal activity is nearly lost for *E. coli*, and entirely lost for *S. aureus*. This result confirms that these compounds can be rendered harmless against bacteria with prolonged exposure to UVA light.

Figure 18:
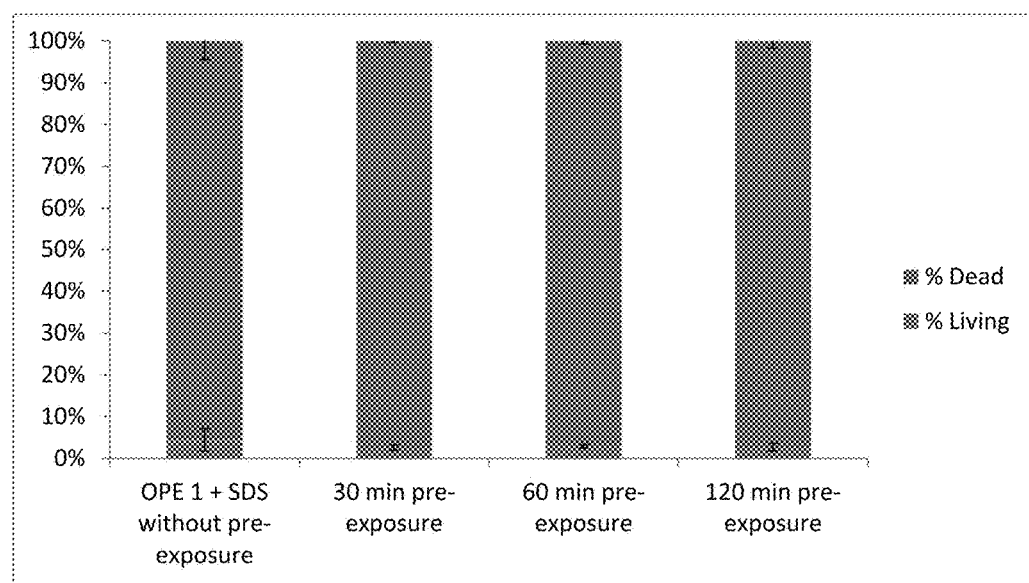
FIG. 18. illustrates biocidal activity of OPE 1-SDS complex vs. *E. coli* with samples irradiated for 0, 30, 60, or 120 minutes prior to bacterial exposure.
Figure 19:
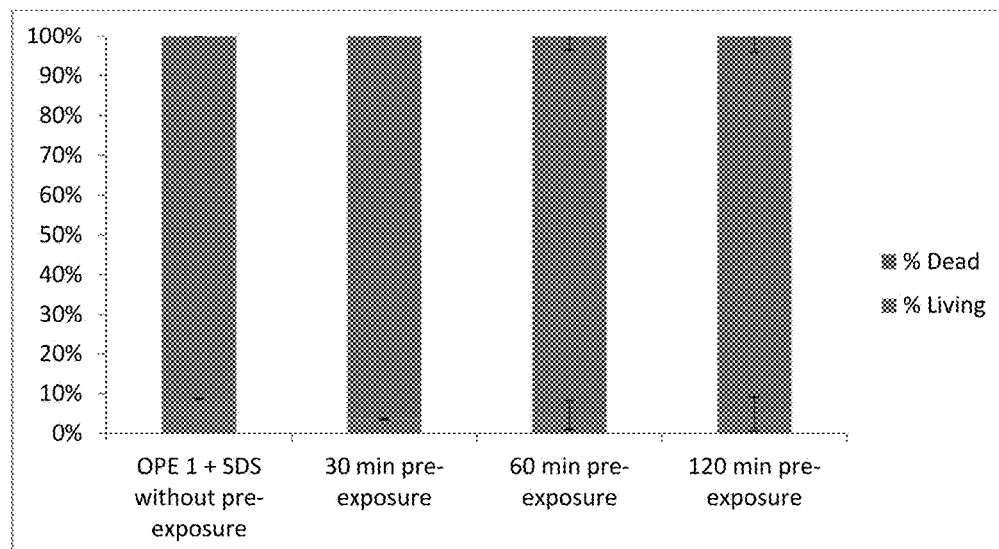
FIG. 19. illustrates biocidal activity of OPE 1-SDS complex vs. *S. Aureus* with samples irradiated for 0, 30, 60, or 120 minutes prior to bacterial exposure.

The bacterial killing of *E. coli* by OPE 1 and SDS as a function of pre-irradiation time is shown in FIG. 18, and the killing of *S. aureus* is shown in FIG. 19.

The results shown in FIGS. 18 and 19 reveal that the OPE 1-SDS complex is able to effectively kill both *S. aureus* and *E. coli* despite prolonged UVA irradiation prior to bacterial exposure. The killing effectiveness of both *E. coli* and *S. aureus* was maintained at more than 95%, even after two hours of irradiation. This result is significant, as it supports the use of molecular self-assembly of surfactants onto oligo-phenylene ethynylenes to confer resistance to photo-degradation. The structure of the aggregate can be an H-aggregate with interfacial water removed by the interaction with the hydrocarbon tails of SDS. SDS does not absorb light in the UVA region, nor should it react with singlet-oxygen that is produced. Thus, complexation with SDS allows the oligo-phenylene ethynylenes to maintain their biocidal activity while being protected from photolysis.

It should be noted that while SDS itself is bactericidal to both *E. coli* and *S. aureus* at the critical micelle concentration (~8.3 mM; see J. Turro and A. Yekta, *J. Am. Chem. Soc.,* 1978, 100, 5951), a low level of killing is observed at the 40 µM concentrations used for complex formation. In addition, it was observed in the control experiments that the two bacteria exhibit different levels of resistance to SDS. *S. aureus* was observed to be viable in the presence of 0.33 mM SDS, yet this concentration was sufficient to achieve significant killing of *E. coli*. 40 µM SDS killed ~40% of the *E. coli* cells. When comparing *S. aureus* and *E. coli*, it is clear that *S. aureus* is much more resistant of the effects of SDS. In light of this fact and the close relation of Rosenbach *S. aureus* to methicillin-resistant *S. aureus* (MRSA), *S. aureus* serves as a useful model organism for this example as it reveals the biocidal activity of the OPE 1-SDS complex without any bias from killing by SDS.

Figure 20:
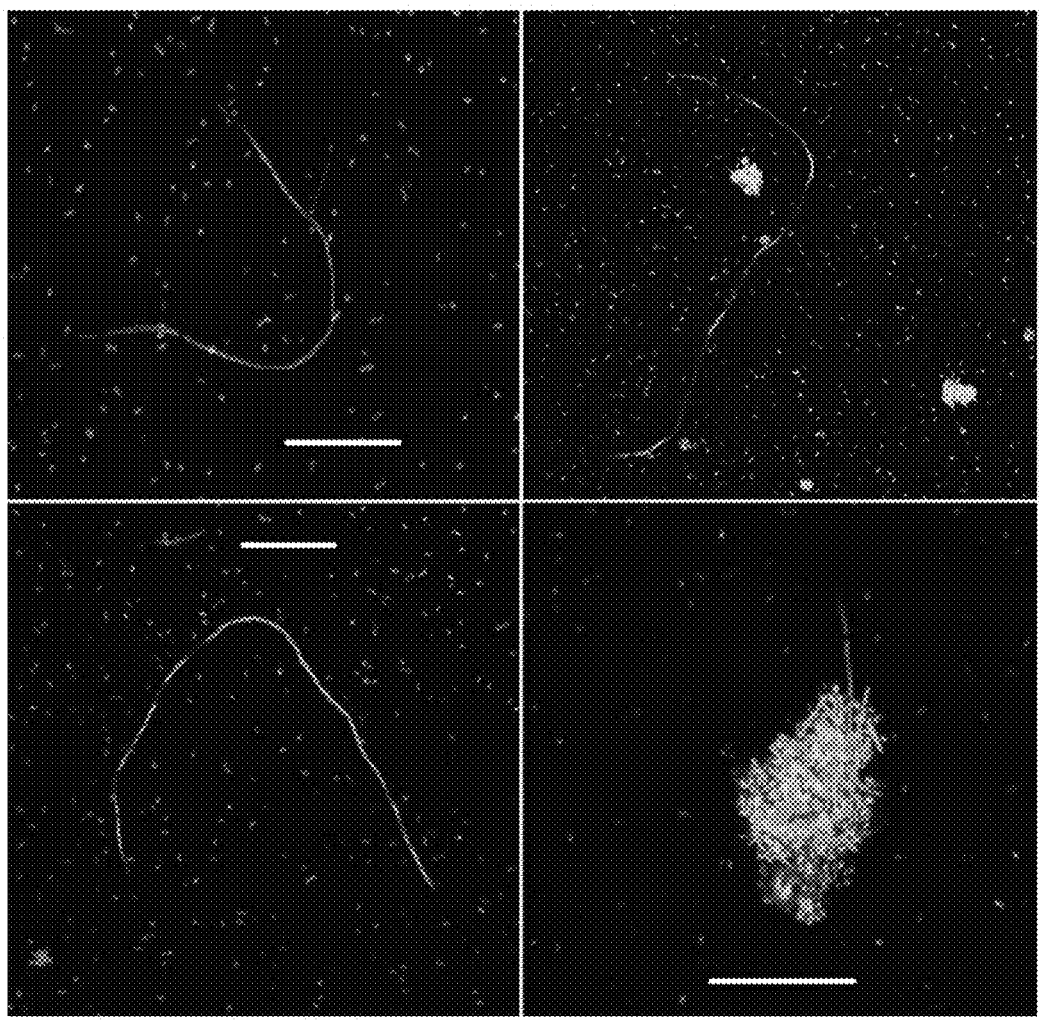
FIG. 20. illustrates filamentous *E. coli* observed upon exposure to OPE 1 or OPE 1-SDS complex; the white line is 20 μM.

While the analysis of *S. aureus* was relatively straightforward, confocal fluorescence microscopy revealed that *E. coli* cells exposed to OPE 1 or OPE 1-SDS were more likely to undergo filamentous growth than untreated cells, as is shown in FIG. 20.

Cell elongation (or filamentation) is a known stress response that *E. coli* is prone to exhibit upon exposure to high heat, antibiotics, and UV irradiation. See, E. Z. Ron and B. D. Davis, *Journal of Bacteriology,* 1971, 107 (1), 391-396; G. N. Rolinson, *Journal of Antimicrobial Chemotherapy,* 1998, 41: 589-603; and P. Burton and I. B. Holland, *Mol Gen Genet.,* 1983, 190(1), 128-32. Due to the lack of frequent occurrence of these filaments in a UVA-treated *E. coli* control, such behavior is attributable to the presence of OPE 1 or OPE 1-SDS. While the mechanism by which these biocides elicit such behavior is not well understood, it is reasonable that the damage caused by the oligo-phenylene ethynylene causes a significant level of oxidative stress and degradation of DNA and proteins, since this has been demonstrated in previous work. see Y. Wang, S. D. Jett, J. Crum, K. S. Schanze, E. Y. Chi and D. G. Whitten, *Langmuir,* 2013, 29 (2), 781-92. Filament growth does not appear to be mitigated by the complexation of OPE 1 with SDS. There are several likely possibilities for the cause of filamentation upon exposure to the biocides, concerning DNA and protein damage caused by reactive oxygen species (ROS).G. Storz and J. A. Imlay, *Current Opinion in Microbiology,* 1999, 2, 188-194; and E. Cabiscol, J. Tamarit and J. Ros, *International Microbiology,* 2000, 3: 3-8. Oxidative stress is known to occur in *E. coli* when the ROS exposure exceeds the capacity of the cell to repair membrane and DNA damage, while still producing proteins to counteract ROS. See T. H. Jones, H.-c. Wong, Editor. *Stress Response of Foodborne Microorganisms* 2012, Nova Science Publishers, 293-330.

Inspection of FIG. 20 reveals several features that indicate specific cellular structures formed by stress responses. The reduced amount of red fluorescence emitting from the filaments indicates that the filaments have taken up less Propidium iodide (dead stain) than the surrounding dead cells. It is important to note that the darker regions of the filament in the top-right image occur as a result of the filaments twisting conformation, causing it to leave the confocal plane. Evidence suggests that the short, dim sections of the filament, such as that indicated by the red arrow in the top-left image, arise from the "Z-ring" formed by FtsZ: an essential division protein that mediates septation. See, for example, R. L. Lock and E. J. Harry, *Nature Reviews Drug Discovery,* 2008, 7, 324-338; S. G. Addinall, C. Cao and J. Lutkenhaus, *Journal of Bacteriology,* 1997, 179 (13), 4277-4284; J. Stricker, P. Maddox, E. D. Salmon and H. P. Erickson, *Proc. Nat. Acad. Sci.,* 2002, 99 (5), 3171-3175; L. Romberg and P. A. Levin, *Annual Review of Microbiology,* 2003, 57, 125-154; D. E. Anderson, F. J. Gueiros-Filho and H. P. Erickson, *Journal of Bacteriology,* 2004, 186 (17), 5775-5781; N. W. Goehring and J. Beckwith, *Current Biology,* 2005, 15, R514-R526; A. I. Rico, M. Garcia-Ovalle, P. Palacios, M. Casanova and M. Vicente, *Molecular Microbiology,* 2010, 76 (3), 760-771. FtsZ generally occupies regions of septation, where cell division is to occur. Due to its importance in bacterial cell division, FstZ serves as a target for broad-spectrum antimicrobials, largely due to a lack of homology with human proteins. See R. L. Lock and E. J. Harry, *Nature Reviews Drug Discovery,* 2008, 7, 324-338. Oxidative stress incurred by the presence of OPE 1 can be sufficient to elicit a depletion of guanosine-5'-triphosphate (GTP), which in turn can reduce the amount of active FtsZ. A lack of FtsZ has been attributed to the formation of filamentous cells. See T. H. Jones, H.-c. Wong, Editor. *Stress Response of Foodborne Microorganisms* 2012, Nova Science Publishers, 293-330. An interesting feature that has been observed in several filaments is the occurrence of helical-shaped patterns within the filament that are brightly-stained with SYTO-21. Two images of these structures are shown below, in FIG. 21.

Figure 21:
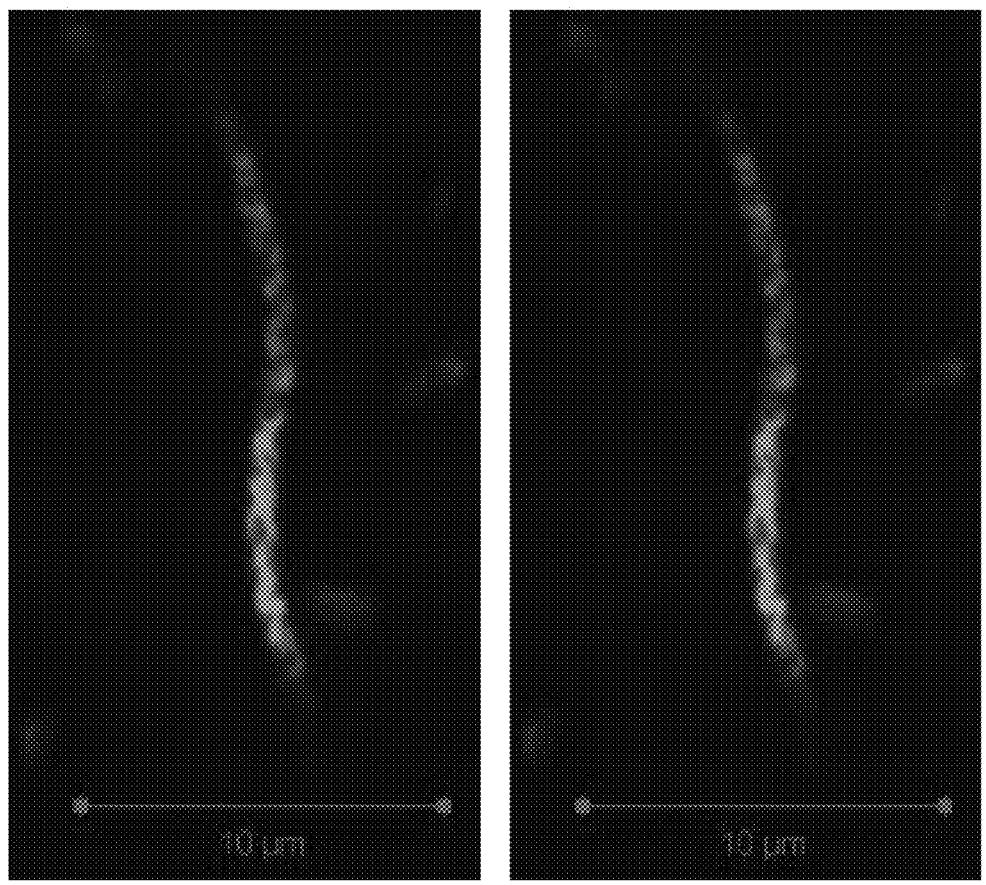
FIG. 21. illustrates helical structures within filamentous *E. coli*.

Though both SYTO-21 and Propidium iodide are nucleic acid stains, the helical structures shown in FIG. 21, resemble several previously observed structures of different cell-division proteins. MreB (an actin homolog) also maintains a helical structure similar to that seen in the left panel of FIG. 21, and damage of this protein has been shown to induce filamentation. See T. Kruse, J. Møller-Jensen, A. Løbner-Olesen and K. Gerdes *EMBO J.,* 2003, 22 (19), 5283-5292.

In recent work, it has been shown that specific genetic mutations can give rise to elongated cells. See M. Maciąg-Dorszyńska, M. Ignatowska, L. Jannière, G.

Węegrzyn and A. Szalewska-Palasz, *Gene*, 2012, 503, 31-35. Filament formation may also be induced by oxidative DNA damage resulting in the SOS response, in which the protein SulA prevents cell division and further chromosome damage. See N. W. Goehring and J. Beckwith, *Current Biology*, 2005, 15, R514-R526. Boeneman et al. observed similar helical structures to those in the left panel of FIG. 8 in *E. coli* by tracking GFP-labeled DnaA protein, which is responsible for initiating chromosomal replication during a filamentous phase of growth. See K. Boeneman, S. Fossum, Y. Yang, N. Fingland, K. Skarstad and E. Crooke, *Molecular Microbiology*, 2009, 72, 645-657. Another protein that may induce DNA into a helical structure, RecA, is responsible for DNA repair during the SOS response and has a strong tendency to bind with ssDNA in a filament formation. As the complex with SDS does significant killing and induces the same signs of stress as the an oligo-phenylene ethynylene alone, it must only benefit from the photo-protection offered by the SDS.

The damage caused by irradiation of *S. Aureus* in the presence of OPE 1 leads to clusters of large numbers of cells. Confocal microscopy images of *S. Aureus* irradiated with UVA light for 15 minutes in the presence of OPE 1 are shown in FIG. 22.

Figure 22:
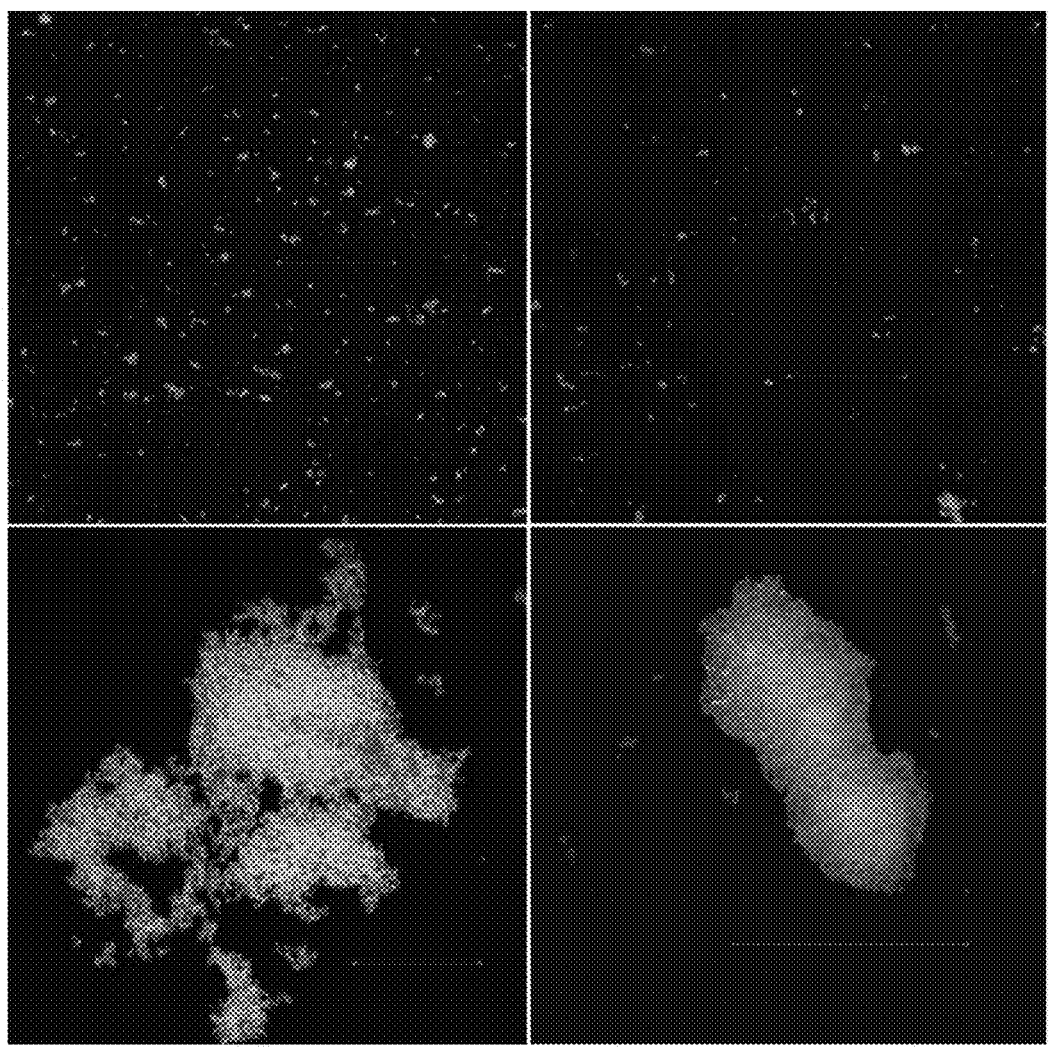
FIG. 22. illustrates confocal microscopy images of *S. Aureus*, where red and yellow indicate dead bacteria and green indicates live bacteria. The red line indicates 50 μM. Top-left: Negative control; Top-right: SDS control; Bottom-left: OPE 1 without SDS; Bottom-right: OPE 1 with SDS.

In FIG. 22, in the top row of images, it can be seen that *S. Aureus* irradiated without OPE 1 formed clusters of ~10 bacteria. In the bottom panel of FIG. 22, it can be seen that large numbers of dead bacteria have agglomerated to form massive clusters, some larger than 100 μM in diameter. These clusters can be indicative of the initial stages of biofilm formation. Biofilm formation in *S. Aureus* is a response to environmental stress and has been shown to be caused by UV exposure, metal toxicity, acid exposure, dehydration and salinity, phagocytosis, and several antibiotics and antimicrobial agents. See G. M. Teitzel and M. R. Parsek, *Applied and Environmental Microbiology*, 2003, 69 (4), 2313-2320; K. McNeill and I. R. Hamilton, *FEMS Microbiology Letters*, 2003, 221, 25-30; E. Le Magrex-Debar, J. Lemoine, M.-P. Gene', L.-F. Jacquelin and C. Choisy *Food Microbiology*, 2000, 55, 239-243; J. G. Leid, M. E. Shirtliff, J. W. Costerton and P. Stoodley, *Infection and Immunity*, 2002, 70 (11), 6339-6345; P. S. Stewart and J. W. Costerton, *Lancet*, 2001, 358 (9276), 135-8; P. Gilbert, D. G. Allison and A. J. McBain, *J Appl Microbiol.*, 2002, 92 Suppl, 98S-110S; T. F. Mah and G. A. O'Toole, *Trends in Microbiology*, 2001, 9 (1), 34-39.

Biofilm formation is both a stress-response and a result of released cell contents inducing adhesion between cells. The formation of *S. aureus* biofilms has been shown to be dependent on cell-lysis, so it stands to reason that the light-activated damage caused by OPE 1 can induce such a response. See E. E. Mann, K. C. Rice, B. R. Boles, J. L. Endres, D. Ranjit, L. Chandramohan, L. H. Tsang, M. S. Smeltzer, A. R. Horswill and K. W. Bayles, *PLOS One*, 2009, 4 (6), e5822; K. C. Rice, E. E. Mann, J. L. Endres, E. Weiss, J. E. Cassat, M. S. Smeltzer and K. W. Bayles, *Proc. Nat. Acad. Sci.*, 2007, 104 (19), 8113-8118; S. E. Cramton, C. Gerke, N. F. Schnell, W. W. Nichols and F. Götz, *Infect Immun.*, 1999, 67 (10), 5427-33. It has also been suggested that DNA, proteins, and other cell contents play an important role in the initial aggregation of the cells. See H. C. Flemming and J. Wingender, *Nat Rev Microbiol.*, 2010, 8 (9), 623-33. It has been previously shown by Ying Wang and coworkers that the cells can be emptied as a result of the damage inflicted on the cell membrane. See Y. Wang, S. D. Jett, J. Crum, K. S. Schanze, E. Y. Chi and D. G. Whitten, *Langmuir*, 2013, 29 (2), 781-92. It is likely that the DNA and proteins emptied from the cells induce the initial aggregation between cells that leads to these large clusters. In the bottom-right panel and the top of the bottom-left panel of FIG. 22, it can be seen that some of the clusters observed have an abundance of dead bacteria on the periphery of the cluster, while fewer dead bacteria are found in the center of the cluster. This is consistent with results observed in previous studies of *S. Aureus* biofilms. See E. E. Mann, K. C. Rice, B. R. Boles, J. L. Endres, D. Ranjit, L. Chandramohan, L. H. Tsang, M. S. Smeltzer, A. R. Horswill and K. W. Bayles, *PLOS One*, 2009, 4 (6), e5822.

OPE 1, alone, was shown to lose biocidal activity with prolonged exposure to UVA light, leading to an ineffective composition of non-biocidal photoproducts. The mixing of cationic oligo-phenylene ethynylenes with the anionic surfactant sodium dodecyl sulfate forms a complex, which has drastically reduced photoreactivity, but retains high light-activated biocidal activity against both Gram-negative and Gram-positive bacteria. Confocal microscopy revealed evidence of filamentous *E. coli* formation, which was attributed to oxidative stress or protein damage caused by the oligo-phenylene ethynylene. A different type of stress response was seen in *S. aureus*, where large clusters of bacteria resembling the initial formation of a biofilm occurred with UVA exposure in the presence of OPE 1.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

What is claimed is:
1. A method of inactivating a microorganism, the method comprising:

contacting the microorganism with an effective amount or concentration of a composition comprising a charged singlet-oxygen sensitizer of the formula IV:

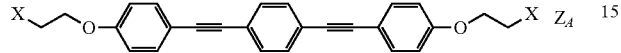

wherein at each occurrence X is independently selected from:

(a)

(b)

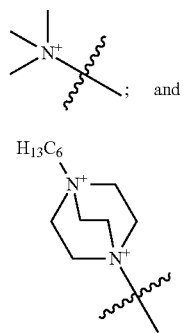

wherein a wavy line indicates a point of bonding, $Z_A$ signifies two or more charge-balancing counterions, and wherein the charge-balancing counterions comprise a sulfate or sulfonate anionic surfactantant.

2. The method of claim 1, wherein the microorganism comprises at least one of a bacterium, virus, fungus, mold, slime mold, algae, and yeast.

3. The method of claim 2, wherein the inactivating continues for a longer period of time than does inactivating under comparable conditions but in the absence of the oppositely-charged surfactant.

4. The method of claim 1, wherein the method is a method of disinfecting an object, comprising contacting the object with the composition.

5. The method of claim 4, wherein the contacting occurs in solution under irradiation by visible light or ultraviolet light.

6. The method of claim 1, wherein the anionic surfactant comprises sodium dodecylsulfate.

7. A method of prolonging the period of time over which bacteria are inactivated or objects are disinfected by a singlet-oxygen sensitizer, the method comprising irradiating a composition comprising a singlet-oxygen sensitizer of the formula IV with visible or ultraviolet light in the presence of oxygen:

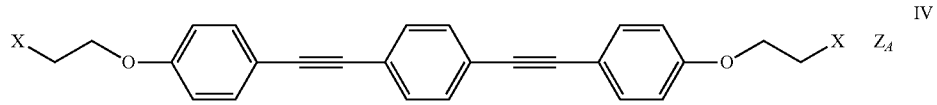

wherein at each occurrence X is independently selected from:

(a)

(b)

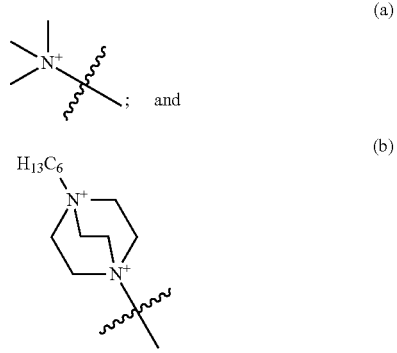

wherein a wavy line indicates a point of bonding, $Z_A$ signifies two or more charge-balancing counterions, and wherein the charge-balancing counterions comprise a sulfate or sulfonate anionic surfactant.

8. A method of enhancing bactericidal properties of a charged singlet-oxygen sensitizer comprising forming a composition comprising the charged singlet-oxygen sensitizer of the formula IV:

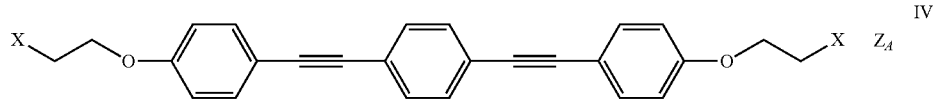

wherein at each occurrence X is independently selected from:

(a)

(b)

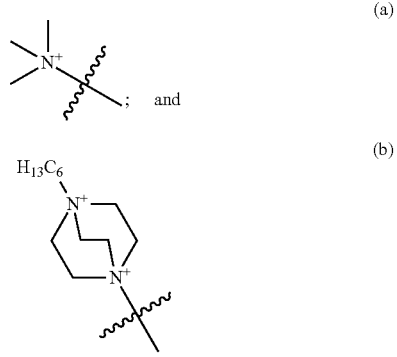

wherein a wavy line indicates a point of bonding, $Z_A$ signifies two or more charge-balancing counterions, and wherein the charge-balancing counterions comprise a sulfate or sulfonate anionic surfactant.

* * * * *

UNITED STATES PATENT AND TRADEMARK OFFICE
CERTIFICATE OF CORRECTION

Page 1 of 2

PATENT NO. : 9,968,698 B2
APPLICATION NO. : 14/533612
DATED : May 15, 2018
INVENTOR(S) : Whitten et al.

It is certified that error appears in the above-identified patent and that said Letters Patent is hereby corrected as shown below:

On the Title Page

In Column 2, item (56) under "Other Publications", Line 9, delete "Actino" and insert --Action-- therefor On page 3, in Column 1, item (56) under "Other Publications", Line 10, delete "hat" and insert --that-- therefor On page 3, in Column 1, item (56) under "Other Publications", Line 42, delete "?laments"," and insert --filaments",-- therefor On page 3, in Column 2, item (56) under "Other Publications", Line 59, delete "tTreatment" and insert --Treatment-- therefor On page 4, in Column 2, item (56) under "Other Publications", Lines 1-2, delete "seggregation" and insert --segregation-- therefor On page 4, in Column 2, item (56) under "Other Publications", Line 17, delete "Bio?lms"," and insert --Biofilms",-- therefor On page 4, in Column 2, item (56) under "Other Publications", Line 34, delete "anibiotics"," and insert --antibiotics",-- therefor On page 4, in Column 2, item (56) under "Other Publications", Line 48, delete "bio?lms"," and insert --biofilms",-- therefor On page 4, in Column 2, item (56) under "Other Publications", Line 63, delete "bio¢lm" and insert --biofilm-- therefor Signed and Sealed this
Eighteenth Day of February, 2020

Andrei Iancu
*Director of the United States Patent and Trademark Office*

CERTIFICATE OF CORRECTION (continued)
U.S. Pat. No. 9,968,698 B2

On page 4, in Column 2, item (56) under "Other Publications", Line 66, delete "a"Turn-on" and insert --a "Turn-on"-- therefor On page 4, in Column 2, item (56) under "Other Publications", Line 67, delete "Polymer," and insert --Polymer",-- therefor On page 5, in Column 1, item (56) under "Other Publications", Line 20, delete "Abilitty" and insert --Ability-- therefor On page 5, in Column 1, item (56) under "Other Publications", Line 45, delete "Lomitation" and insert --Limitation-- therefor On page 5, in Column 2, item (56) under "Other Publications", Line 31, delete "Bio?lm" and insert --Biofilm-- therefor On page 6, in Column 1, item (56) under "Other Publications", Line 5, delete "electronc" and insert --electron-- therefor On page 6, in Column 2, item (56) under "Other Publications", Line 4, delete "Bsnd" and insert --Band-- therefor On page 6, in Column 2, item (56) under "Other Publications", Line 8, delete "oligophenyleneethynylenes"," and insert --oligo (phenylene ethynylene)s",-- therefor On page 6, in Column 2, item (56) under "Other Publications", Lines 11-12, delete "Oligo (phenylene ethynylene) s:"," and insert --Oligo(phenylene ethynylene)s:",-- therefor On page 6, in Column 2, item (56) under "Other Publications", Line 24, delete "Acton" and insert --Action-- therefor In the Claims In Column 23, Line 2, in Claim 1, after "comprising", insert --:--

In Column 23, Line 40 (Approx.), in Claim 1, delete "surfactantant." and insert --surfactant.-- therefor